US010684291B2

(12) United States Patent
Block et al.

(10) Patent No.: US 10,684,291 B2
(45) Date of Patent: Jun. 16, 2020

(54) BIOMARKERS FOR RISK ASSESSMENT AND TREATMENT MONITORING IN HEART FAILURE PATIENTS GUIDED BY NATRIURETIC PEPTIDES

(71) Applicant: Roche Diagnostics Operations, Inc., Indianapolis, IN (US)

(72) Inventors: Dirk Block, Bichl (DE); Hans-Peter Brunner, Muenchenstein (CH); Ursula-Henrike Wienhues-Thelen, Krailling (DE); Christian Zaugg, Rheinfelden (CH); Thomas Dieterle, Freiburg (DE); Cheryl Mitchell, Tucson, AZ (US); Johan Ubby, Zug (CH); Sandra Sanders-van Wijk, Maastricht (NL)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

(21) Appl. No.: 15/220,555

(22) Filed: Jul. 27, 2016

(65) Prior Publication Data
US 2016/0334419 A1  Nov. 17, 2016

Related U.S. Application Data

(63) Continuation of application No. PCT/EP2015/051239, filed on Jan. 22, 2015.

(30) Foreign Application Priority Data

Jan. 28, 2014 (EP) .................................. 14152777

(51) Int. Cl.
G01N 33/53 (2006.01)
G01N 33/68 (2006.01)
G01N 33/62 (2006.01)
G01N 33/66 (2006.01)
G01N 33/70 (2006.01)
G01N 33/72 (2006.01)
G01N 33/84 (2006.01)

(52) U.S. Cl.
CPC ......... *G01N 33/6893* (2013.01); *G01N 33/62* (2013.01); *G01N 33/66* (2013.01); *G01N 33/6869* (2013.01); *G01N 33/6887* (2013.01); *G01N 33/70* (2013.01); *G01N 33/723* (2013.01); *G01N 33/84* (2013.01); *G01N 2333/4737* (2013.01); *G01N 2333/5412* (2013.01); *G01N 2333/58* (2013.01); *G01N 2333/78* (2013.01); *G01N 2333/805* (2013.01); *G01N 2800/325* (2013.01); *G01N 2800/347* (2013.01); *G01N 2800/52* (2013.01)

(58) Field of Classification Search
None
See application file for complete search history.

(56) References Cited

U.S. PATENT DOCUMENTS

| 4,016,043 A | 4/1977 | Schuurs et al. |
| 4,018,653 A | 4/1977 | Mennen |
| 4,424,279 A | 1/1984 | Bohn et al. |
| 5,695,761 A | 12/1997 | Denhardt et al. |
| 5,744,305 A | 4/1998 | Fodor et al. |
| 5,804,452 A * | 9/1998 | Pronovost ................ C12Q 1/26 422/420 |
| 6,414,219 B1 | 7/2002 | Denhardt et al. |
| 6,709,855 B1 | 3/2004 | Stanton et al. |
| 2005/0032879 A1* | 2/2005 | Okarter ............... A61K 31/137 514/423 |
| 2006/0003338 A1 | 1/2006 | Deng et al. |
| 2009/0197900 A1 | 8/2009 | Dittrich |

FOREIGN PATENT DOCUMENTS

| WO | 1999/006445 A1 | 2/1999 | |
| WO | 2000/070051 A1 | 11/2000 | |
| WO | 2002/083913 A1 | 10/2002 | |
| WO | 2002/089657 A2 | 11/2002 | |
| WO | 2005/060652 A2 | 7/2005 | |
| WO | 2005/113585 A2 | 12/2005 | |
| WO | 2008/015254 A2 | 2/2008 | |
| WO | WO-2008089994 A1 * | 7/2008 | ......... G01N 33/6893 |
| WO | 2009/141374 A1 | 11/2009 | |

(Continued)

OTHER PUBLICATIONS

Hammerer-Lercher et al., Analysis of Circulating Forms of proBNP and NT-proBNP in Patients with Severe Heart Failure, Clin. Chem. (2008), 54(5), p. 858-865.*
Qi et al., Effects of different peptide fragments derived from proadrenomedullin on gene expression of adrenomedullin gene, Peptides, (2002), 23, p. 1141-1147.*
Abdelsalam et al., Correlation between urea level and HbA1C level in type 2 diabetic patients, Sudan Medical Laboratory Journal, 2011; 1(2), pp. 1-6.*
Abdollahi, Amir et al., Endostatin's Antiangiogenic Signaling Network, Molecular Cell, 2004, pp. 649-663, vol. 13.

(Continued)

*Primary Examiner* — Gary Counts
(74) *Attorney, Agent, or Firm* — Roche Diagnostics Operations, Inc.

(57) ABSTRACT

The present description relates to a method for identifying a patient who is eligible for an intensification of heart failure therapy. Furthermore, the description relates to a method for optimizing B type natriuretic peptide (BNP) and/or N-terminal pro B-type natriuretic peptide (NT-proBNP)-type peptide guided heart failure therapy. The methods are based on the measurement of the level of at least one marker in a sample from a patient who has heart failure and who receives B-type natriuretic peptide (BNP) and/or N-terminal pro B-type natriuretic peptide (NT-proBNP)-type peptide guided heart failure therapy. Further described are kits and devices adapted to carry out the described method.

10 Claims, No Drawings

(56) References Cited

FOREIGN PATENT DOCUMENTS

| WO | 2010/124821 A1 | 11/2010 |
|---|---|---|
| WO | 2010/125165 A1 | 11/2010 |
| WO | 2011/012268 A1 | 2/2011 |
| WO | 2012/106152 A1 | 8/2012 |

OTHER PUBLICATIONS

Akaogi, Kotaro et al., Specific accumulation of tumor-derived adhesion factor in turmor blood vessels and in capillary tube-like structures of cultured vascular endothelial cells, Proceedings of the National Academy of Sciences USA, 1996, pp. 8384-8389, vol. 96.
Ameye, Laurent and Young, Marian F., Mice deficient in small leucine-rich proteoglycans: novel in vivo models for osteoporosis, osteoarthritis, Ehlers-Danlos syndrome, muscular dystrophy, and corneal diseases, Glycobiology, 2002, pp. 107R-116R, vol. 12, No. 9.
Baek, Seung Joon et al., Cyclooxygenase Inhibitors Regulate the Expression of a TGF-β Supertamily Member That Has Proapoptotic and Antitumorigenic Activities, Molecular Pharmacology, 2001, pp. 901-908, vol. 59, No. 4.
Bartels, H. et al., Serum Kreatininbestimmung Ohne Enteiseissen, Clinica Chimica Acta, 1972, pp. 193-197, vol. 37, English Abstract.
Bauskin, Asne R. et al., The propeptide of macrophage inhibitory cytokine (MIC-1), a TGF-β superfamily member, acts as a quality control determinant for correctly folded MIC-1, The EMBO Journal, 2000, pp. 2212-2220, vol. 19, No. 10.
Bonow, Robert O., New Insights Into the Cardiac Natriuretic Peptides, Circulation, 1996, pp. 1946-1950, vol. 93.
Bootcov, Michelle R. et al., MIC-1, a novel macrophase inhibitory cytokine, is a divergent member of the TGF-β superfamily, Proceedings of the National Academy of Sciences USA, 1997, pp. 11514-11519, vol. 94.
Burger, Angelika M. et al., Down-regulation of T1A12/mac25, a novel insulin-like growth factor binding protein related gene, is associated with disease progression in breast carcinomas, Oncogene, 1998, pp. 2459-2467, vol. 15.
Böttner, Martina et al., Characterization of the rat, mouse, and human genes of growth/differentiation factor-15/macrophage inhibiting cytokine-1 (GDF-15/MIC-1), Gene, 1999, pp. 105-111, vol. 237.
De Filippi, Christopher R. et al., Clinical Validation of a Novel Assay for Galectin-3 for Risk Assessment in Acutely Destabilized Heart Failure, The 13th Annual Scientific Meeting HFSA, 2009, p. S9, Abstract 020.
Denhardt, David T. and Guo, Xiaojia, Osteopontin: a protein with diverse functions, FASEB Journal, 1993, pp. 1475-1482, vol. 7.
Dickstein, Kenneth et al., ESC Guidelines for the diagnosis and treatment of acute and chronic heart failure 2008, European Heart Journal, 2008, pp. 2388-2442, vol. 29.
Dieplinger, Benjamin et al., Long-term stability of soluble ST2 in frozen plasma samples, Clinical Biochemistry, 2010, pp. 1169-1170, vol. 43.
Giachelli, Cecilia M. et al., Molecular and Cellular Biology of Osteopontin, Trends in Cardiovascular Medicine, 1995, pp. 88-95, vol. 5, No. 3.
Hromas, Robert et al., PLAB, a novel placental bone morphogenetic protein, Biochimica et Biophysica Acta, 1997, pp. 40-44, vol. 1354.
Hunt, Sharon A. et al., ACC/AHA Guidelines for the Evaluation and Management of Chronic Heart Failure in the Adult: Executive Summary, Journal of the American College of Cardiology, 2001, pp. 2101-2113, vol. 38, No. 7.
Hunt, Sharon Ann et al., ACC/AHA 2005 Guideline Update for the Diagnosis and Management of Chronic Heart Failure in the Adult, Journal of the American College of Cardiology, 2005, pp. e1-e82, vol. 46.
Hwa, Vivian et al., The Insulin-Like Growth Factor-Binding Protein (IGFBP) Superfamily, Endocrine Reviews, 1999, pp. 761-787, vol. 20, No. 6.
International Search Report dated Apr. 30, 2015, in Application No. PCT/EP2015/051239, 6 pages.
Irby, R. B. et al., Osteopontin regulates multiple functions contributing to human colon cancer development and progression, Clinical & Experimental Metastasis, 2004, pp. 515-523, vol. 21.
Januzzi, James L., Jr., The role of natriuretic peptide testing in guiding chronic heart failure management: Review of available data and recommendations for use, Archives of Cardiovascular Disease, 2012, pp. 40-50, vol. 105.
Jones, John I. and Clemmons, David R., Insulin-Like Growth Factors and Their Binding Proteins: Biological Actions, Endocrine Reviews, 1995, pp. 3-34, vol. 16, No. 1.
Karl, J. et al., Development of a novel, N-Terminal-proBNP (NT-proBNP) assay with a low detection limit, Scandinavian Journal of Clinical & Laboratory Investigation Supplement, 1999, pp. 177-181, vol. 59, Supplement 230.
Kiefer, Michael C. et al., The cDNA and derived amino acid sequence for human osteopontin, Nucleic Acids Research, 1989, p. 3306, vol. 17.
Kim, Ho-Seong et al., Identification of a family of low-affinity insulin-like growth factor binding proteins (IGFBPs): Characterization of connective tissue growth factor as a member of the IGFBP superfamily, Proceedings of the National Academy of Sciences USA, 1997, pp. 12981-12986, vol. 94.
Kistorp, Caroline et al., N-Terminal Pro-Brain Natriuretic Peptide, C-Reactive Protein, and Urinary Albumin Levels as Predictors of Mortality and Cardiovascular Events in Older Adults, JAMA, 2005, pp. 352-358, vol. 293, No. 13.
Lawton, Lee N. et al., Identification of a novel member of the TGF-beta superfamily highly expressed in human placenta, Gene, 1997, pp. 17-26, vol. 203.
López-Bermejo, Abel et al., Generation of Anti-Insulin-Like Growth Factor-Binding Protein-Related Protein 1 (IGFBP-rP1/MAC25) Monoclonal Antibodies and Immunoassay: Quantification of IGFBP-rP1 in Human Serum and Distribution in Human Fluids and Tissues, The Journal of Clinical Endocrinology & Metabolism, 2003, pp. 3401-3408, vol. 88, No. 7.
López-Bermejo, Abel et al., Insulin Resistance Is Associated With Increased Serum Concentration of IGF-Binding Protein-Related Protein 1 (IGFBP-rP1/MAC25), Diabetes, 2006, pp. 2333-2339, vol. 55.
Maeder, Micha T. et al., Incidence, clinical predictors, and prognostic impact of worsening renal function in elderly patients with chronic heart failure on intensive medical therapy, American Heart Journal, 2012, pp. 407-414.e1, vol. 163, No. 3.
Miyata, Masaaki et al., Comparative study of therapeutic effects of short- and long-acting loop diuretics in outpatients with chronic heart failure (COLD-CHF), Journal of Cardiology, 2012, pp. 352-358, vol. 59.
Morrish, D. W. et al., Identification by Subtractive Hybridization of a Spectrum of Novel and Unexpected Genes Associated with In Vitro Differentiation of Human Cytotrophoblast Cells, Placenta, 1996, pp. 431-441, vol. 17.
Mueller, Thomas et al., Head-to-head comparison of the diagnostic utility of BNP and NT-proBNP in symptomatic and asymptomatic structural heart disease, Clinica Chimica Acta, 2004, pp. 41-48, vol. 341.
Mueller, Thomas et al., Long-term stability of endogenous B-type natriuretic peptide (BNP) and amino terminal proBNP (NT-proBNP) in frozen plasma samples, Clinical Chemistry & Laboratory Medicine, 2004, pp. 942-944, vol. 42, No. 8.
Needleman, Saul B. and Wunsch, Christian D., A General Method Applicable to the Search for Similarities in the Amino Acid Sequence of Two Proteins, Journal of Molecular Biology, 1970, pp. 443-453, vol. 48.
Nolan, John P. and Sklar, Larry A., Suspension array technology: evolution of the flat-array paradigm, TRENDS in Biotechnology, 2002, pp. 9-12, vol. 20, No. 1.
O'Reilly, Michael S. et al., Endostatin: An Endogenous Inhibitor of Angiogenesis and Tumor Growth, Cell, 197, pp. 277-285, vol. 88, 1997.

(56) References Cited

OTHER PUBLICATIONS

Oh, Youngman et al., Synthesis and Characterization of Insulin-like Growth Factor-binding Protein (IGFBP)-7, The Journal of Biological Chemistry, 1996, pp. 30322-30325, vol. 271, No. 48.

Oldberg, Åke et al., Cloning and sequence analysis of rat bone sialoprotein (osteopontin) cDNA reveals an Arg-Gly-Asp cell-binding sequence, Proceedings of the National Academy of Sciences USA, 1986, pp. 8819-8823, vol. 83.

Oldberg, Åke et al., Identification of a Bone Sialoprotein Receptor in Osteosarcoma Cells, The Journal of Biological Chemistry, 1988, pp. 19433-19436, vol. 263, No. 38.

Ono, Yasuhiro et al., Expression of prostacyclin-stimulating factor, a novel protein, in tissues of Wistar rats and in cultured cells, Biochemical and Biophysical Research Communications, 1994, pp. 1490-1496, vol. 202, No. 3.

Ortega, Nathalie and Werb, Zena, New functional roles for non-collagenous domains of basement membrane collagens, Journal of Cell Science, 2002, pp. 4201-4214, vol. 115.

Paralkar, Vishwas M. et al., Cloning and Characterization of a Novel Member of the Transforming Growth Factor-β/Bone Morphogenetic Protein Family, The Journal of Biological Chemistry, 1998, pp. 13760-13767, vol. 273, No. 22.

Pearson, Thomas A. et al., Markers of Inflammation and Cardiovascular Disease Application to Clinical and Public Health Practice A Statement for Healthcare Professionals From the Centers for Disease Control and Prevention and the American Heart Association, Circulation, 2003, pp. 499-511, vol. 107.

Pearson, William R. and Lipman, David J., Improved tools for biological sequence comparison, Proceedings of the National Academy of Sciences USA, 1988, pp. 2444-2448, vol. 85.

Praetorius, E. and Poulsen, H., Enzymatic Determination of Uric Acid with Detailed Directions, Scandinavian Journal of Clinical and Laboratory Investigation, 1953, pp. 273-280, vol. 5, No. 3.

Richter, Mark M., Electrochemiluminescence (ECL), Chemical Reviews, 2004, pp. 3003-3036, vol. 104.

Sanders-Van Wijk, Sandra et al, Safety and tolerability of intensified, N-terminal pro brain natriuretic peptide-guided compared with standard medical therapy in elderly patients with congestive heart failure: results from TIME-CHF, European Journal of Heart Failure, 2013, pp. 910-918, vol. 15, No. 8.

Shah, Monica R. et al., The STARBRITE Trial: A Randomized, Pilot Study of B-Type Natriuretic Peptide-Guided Therapy in Patients With Advanced Heart Failure, Journal of Cardiac Failure, vol. 17, No. 8, pp. 613-621.

Smith, M. W. et al., Delayed metabolism of human brain natriuretic peptide reflects resistance to neutral andopeptidase, Journal of Endocrinology, 2000, pp. 239-246, vol. 167.

Smith, Temple F. and Waterman, Michael S., Comparison of Biosequences, Advances in Applied Mathematics, 1981, pp. 482-489, vol. 2.

Sprenger, Cynthia C. et al., Insulin-like Growth Factor Binding Protein-related Protein 1 (IGFBP-rP1) Is a Potential Tumor Suppressor Protein for Prostate Cancer, Cancer Research, 1999, pp. 2370-2375, vol. 50.

St. Croix, Brad et al., Genes Expressed in Human Tumor Endothelium, Science, 2000, pp. 1197-1202, vol. 289.

Tan, Mingjia et al., PTGF-β, a type β transforming growth factor (TGF-β) superfamily member, is a p53 target gene that inhibits tumor cell growth via TGF-β signaling pathway, Proceedings of the National Academy of Sciences, 2000, pp. 109-114, vol. 97, No. 1.

Tasheva, Elena S. et al., Mimecan/osteoglycin-deficient mice have collagen fibril abnormalities, Molecular Vision, 2002, pp. 407-415, vol. 8.

Teerlink, John R., Diagnosis and Management of Acute Heart Failure, Braunwald's Heart Disease A Textbook of Cardiovascular Medicine, 2008, Chapter 24, pp. 583-610, Eighth Edition, Saunders Elsevier, Philadelphia, PA.

Town, Michael-Harold et al., A Sensitive Colorimetric Method for the Enzymatic Determination of Uric Acid, Journal of Clinical Chemistry & Clinical Biochemistry, 1985, p. 591, vol. 23, No. 9.

Woo, Patricia et al., Characterization of Genomic and Complementary DNA Sequence of Human C-reactive Protein, and Comparison with the Complementary DNA Sequence of Serum Amyloid P Component, The Journal of Biological Chemistry, 1985, pp. 13384-13388, vol. 260, No. 24.

Wu, Alan H. B. et al., Analytical and Clinical Evaluation of the Bayer ADVIA Centaur Automated B-Type Natriuretic Peptide Assay in Patients with Heart Failure: A Multisite Study, Clinical Chemistry, 2004, pp. 867-873, vol. 50, No. 5.

Yeh, Edward T. H., CRP as a Mediator of Disease, Circulation, 2004, pp. II-11-II-14, vol. 109 [suppl II].

Yeo, Kiang-Teck J. et al., Multicenter evaluation of the Roche NT-proBNP assay and comparison to the Biosite Triage BNP assay, Clinica Chimica Acta, 2003, pp. 107-115, vol. 338.

Yokoyama-Kobayashi, Midori et al., Human cDNA Encoding a Novel TGF-β Superfamily Protein Highly Expressed in Placenta, Journal of Biochemistry, 1997, pp. 622-626, vol. 122, No. 3.

Foster-Swanson, A. et al., Reference Interval Studies of the Rate-Blanked Creatinine/Jaffé Method on BM/Hitachi Systems in Six U.S. Laboratories, Clinical Chemistry, 1994, p. 1057, Abstract 0361, vol. 40, No. 6, English portions only.

Popper, Hans et al., Zur Kreatininbestimmung im Blute, Biochemische Zeitschrift, 1937, pp. 354-357, vol. 291, English portions only.

Schmidt, F. H., Die enzymatische Bestimmung von Glucose and Fructose nebeneinander, Klinische Wochenzeitschrift, 1961, pp. 1244-1247, vol. 39, English portions only.

Seelig, H. P. and Wüst, H., Die Kreatinbestimmung mit der Jaffé Reaktion, Ärztliches Labor, 1969, pp. 34-39, English Summary, vol. 15, English portions only.

Januzzi, James L., Jr., Use of Biomarkers to "Guide" Care in Chronic Heart Failure: What Have We Learned (So Far)?, Journal of Cardiac Failure, 2011, pp. 622-625, vol. 17, No. 8.

Guidelines for Treatment of Acute Heart Failure, Guidelines for Diagnosis and Treatment of Cardiovascular Disease (2004-2005 Joint Working Groups Report), Journal of Cardiac Surgery, 2006, English translation of pp. 50-51, 67 pages, English portions only.

Felker, G. Michael et al., Biomarker-guided therapy in chronic heart failure: A meta-analysis of randomized controlled trials, American Heart Journal, 2009, pp. 422-430, vol. 158, No. 3.

Hochholzer, Willibald et al., Impact of soluble fms-like tyrosine kinase-1 and placental growth factor serum levels for risk stratification and early diagnosis in patients with suspected acute myocardial infarction, European Heart Journal, 2011, pp. 326-335, vol. 32.

Kameda, Ryo et al., Soluble Fms-like Tyrosine Kinase 1 Is a Novel Predictor of Brain Natriuretic Peptide Elevation, International Heart Journal, 2013, pp. 133-139, vol. 54.

Ky, Bonnie et al.., The Vascular Marker Soluble Fms-like Tyrosine Kinase 1 is Associated with Disease Severity and Adverse Outcomes in Chronic Heart Failure, Journal of the American College of Cardiology, 2011, pp. 386-394, vol. 58, No. 4.

\* cited by examiner

BIOMARKERS FOR RISK ASSESSMENT AND TREATMENT MONITORING IN HEART FAILURE PATIENTS GUIDED BY NATRIURETIC PEPTIDES

CROSS REFERENCE TO RELATED APPLICATIONS

This application is a continuation of International Patent Application No. PCT/EP2015/051239 filed Jan. 22, 2015, and claims priority to European Patent Application No. 14152777.0 filed Jan. 28, 2014, the disclosures of which are hereby incorporated by reference in their entirety.

SUMMARY

The present invention relates to a method for identifying a patient who is eligible to an intensification of heart failure therapy. Furthermore, the present invention relates to a method for optimizing BNP-type peptide guided heart failure therapy. The methods are based on the measurement of the level of at least one marker in a sample from a patient who has heart failure and who receives BNP-type peptide guided heart failure therapy. Further envisaged by the present invention are kits and devices adapted to carry out the present invention.

Heart failure (HF) is among the leading causes of morbidity and mortality in many countries worldwide. Although available treatment options can reduce morbidity and mortality in patients with HF, the relative number of eligible patients receiving these treatments remains unsatisfactorily low. Furthermore, in patients eligible for treatment, therapy has been primarily guided and adjusted by signs and symptoms of HF to maximal tolerability of drugs (e.g. by NYHA stages, ACC/AHA stages, or congestion scores).

Measurement of natriuretic peptide markers, such as B-type natriuretic peptide (BNP), or its amino-terminal fragment N-terminal proBNP (NT-proBNP), has emerged as an important tool for the diagnosis and risk stratification of patients with HF. Additionally, there is emerging evidence that NT-proBNP is useful in guiding medical therapy in heart.

NT-proBNP guided HF therapy, however, does not identify all patients at risk of HF decompensation and of adverse events. Consequently, some patients remain at risk even though they show favorable response to therapy with regards to their NT-proBNP levels. And thus, not all patients benefit from intensification of heart failure therapy.

Advantageously, it has been found in the studies underlying the present invention that the combination of NT-proBNP or BNP with other markers and clinical parameters can be used for monitoring purposes and as a guide for therapy in addition to current standard-of-care to adjust and titrate therapy in HF patients (chronic or acute HF after stabilization). These markers and parameters are Creatinine, BUN (urea), Glucose, HbA1c, hsCRP, Cystatin C, IL-6, Prealbumin, sFLt-1, Uric Acid, GDF-15, sST2, Galectin-3, Endostatin, Mimecan, IGFBP-7, Osteopontin, Sodium, Hemoglobin, and Hematocrit, as well as heart rate and QRS duration. Specifically, addition of these measurements to NT-proBNP or BNP together with current standard-of-care are able to further risk stratify HF patients who are already guided by NT-proBNP but may be in need for more intensified therapy and closer observation. Thus, the present invention optimizes heart failure therapy guidance beyond NT-proBNP by considering combinations of natriuretic peptides with other markers and/or clinical parameters.

In particular, it has been found in the studies of the present invention that the additional determination of the markers of parameters as referred to above allows for the identification of a subgroup of patients which display a level of a BNP-type peptide which is below the reference level for said BNP-type peptide indicative for the intensification of heart failure therapy, but which nevertheless are eligible to an intensification of heart failure treatment. Thanks to the present invention, patients can be identified which require an intensification of heart failure therapy which based on the measurement of the level of a BNP-type alone would have not received an intensified heart failure therapy.

Accordingly, the present invention is directed to a method for identifying or selecting a patient who is eligible to an intensification of heart failure therapy, said method comprising the steps of (a) measuring the level of at least one marker selected from the group consisting of creatinine, urea, sodium, glucose, HbA1c (glycated hemoglobin), hemoglobin, hematocrit, CRP (C-reactive protein, in particular high sensitive CRP), Cystatin C, IL-6 (Interleukin 6), Prealbumin, sFlt-1 (soluble fms-like tyrosine kinase-1), uric acid, GDF-15 (Growth Differentiation Factor 15), Galectin-3 (Gal-3), Endostatin, Mimecan, IGFBP7 (Insulin Growth Factor Binding Protein 7), sST2 (soluble ST2), and Osteopontin in a sample from a patient who has heart failure and who receives BNP-type peptide guided heart failure therapy, in particular NT-proBNP guided heart failure therapy or BNP guided heart failure therapy, and (b) comparing the level (or levels) of the marker (or markers) measured in (a) to a reference level (or reference levels).

In an embodiment, the method further comprises step (c) of identifying or selecting a patient who is eligible to an intensification of heart failure therapy, i.e. of BNP-type peptide guided therapy.

In addition, the method may comprise step (d) of intensifying heart failure therapy or recommending intensification of heart failure therapy (if the patient has been identified as to be eligible to intensification of heart failure therapy). Accordingly, the present invention also envisages a method of intensifying heart failure therapy, said method comprising steps (a) to (d) as set forth above.

The method of the present invention, preferably, is an ex vivo or in vitro method. Moreover, it may comprise steps in addition to those explicitly mentioned above. For example, further steps may relate to sample pre-treatments or evaluation of the results obtained by the method. The method may be carried out manually or assisted by automation. Preferably, step (a) and/or (b) may in total or in part be assisted by automation, e.g., by a suitable robotic and sensory equipment for the measurement in steps (a) or a computer-implemented identification in step (c).

In an embodiment the aforementioned method may additionally comprise assessing or providing the QRS duration and the comparison of the thus determined QRS duration to a reference.

Further, it is envisaged to assess or to provide the QRS duration instead of measuring the level of the at least one marker in step a) and to compare the thus determined QRS duration to a reference.

Accordingly, the present invention further envisages a method for identifying or selecting a patient who is eligible to an intensification of heart failure therapy, said method comprising the steps of (a) assessing or providing the QRS duration of a patient who has heart failure and who receives BNP-type peptide guided heart failure therapy, and (b) comparing QRS duration to a reference, wherein a QRS duration which is increased as compared to the reference is indicative for a patient who is eligible to intensification of heart failure therapy, whereas a QRS duration which is decreased as compared to the reference is indicative for a patient who is not eligible to intensification of heart failure therapy The "patient" as referred to herein is, preferably, a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the patient is a human patient. The terms "subject" and "patient" are used interchangeably herein.

The phrase "selecting a patient" or "identifying a patient" as used herein refers to using the information or data generated relating to the level of the at least one marker as referred to in the context of the present invention in a sample of a patient to identify or selecting the patient as more likely to benefit or less likely to benefit from an intensification of heart failure therapy. Preferably, a subject who is eligible to said intensification requires said intensification, whereas a subject who is not eligible to said intensification does not require said intensification.

It is to be understood that a subject who is eligible to intensification of heart failure therapy will benefit from the intensification, whereas a subject who is not eligible to said intensification may not benefit from said intensification, e.g. may experience adverse side-effects or harm from the intensification. In particular, a subject benefits from the intensification, if the intensification reduces the risk of mortality of said subject and/or reduces the risk of hospitalization and/or of cardiac decompensation of said subject, in particular within a window period of 18 months or 3 years after the sample has been obtained. Preferably, the aforementioned risk (or risks) is (are) reduced by 5%, more preferably by 10%, even more preferably by 15% and, most preferably by 20%. Preferably, the hospitalization and mortality referred to herein shall be due to heart failure.

In contrast, a subject who is not eligible to intensification of heart failure therapy will not benefit (in particular will not benefit significantly) from the intensification. In particular, a subject does not benefit from the intensification, if the intensification does not reduce (in particular, does not reduce significantly) the risk of mortality of said subject and/or does not reduce (in particular, does not reduce significantly) the risk of hospitalization and/or of cardiac decompensation of said subject and/or increases the risk of unwanted side effects, in particular within a window period of 18 months or 3 years after the sample has been obtained. In this case, unnecessary health care costs can be avoided, if the therapy is not intensified. Further, adverse side effects that may result from the intensification can be avoided.

Thus, by identifying a subject who is eligible to intensification of heart failure therapy, it can be assessed whether said subject will benefit from the intensification of heart failure therapy, or not. Accordingly, the present invention also relates to a method of identifying a subject who will benefit from intensification of heart failure therapy, based on the steps set forth herein elsewhere.

The information or data used or generated may be in any form, written, oral or electronic. In some embodiments, using the information or data generated includes communicating, presenting, reporting, storing, sending, transferring, supplying, transmitting, dispensing, or combinations thereof. In some embodiments, communicating, presenting, reporting, storing, sending, transferring, supplying, transmitting, dispensing, or combinations thereof are performed by a computing device, analyzer unit or combination thereof. In some further embodiments, communicating, presenting, reporting, storing, sending, transferring, supplying, transmitting, dispensing, or combinations thereof are performed by a laboratory or medical professional. In some embodiments, the information or data includes a comparison of the level (levels) of the at least one marker to a reference level (or to reference levels).

As described herein below in more detail, a subject who is eligible to intensification of heart failure treatment, shall be also monitored at short intervals, whereas a subject who is not eligible to intensification of heart failure treatment (i.e. who does not require intensification of heart failure treatment) shall be monitored at long intervals. Therefore, in addition to the decision whether heart failure treatment shall be intensified or not, it can be assessed whether the subject shall be monitored at short intervals or long intervals.

DETAILED DESCRIPTION

As will be understood by those skilled in the art, the assessment made by the method of the present invention is usually not intended to be correct for 100% of the subjects to be diagnosed. The term, however, requires that the assessment is correct for a statistically significant portion of the subjects (e.g. a cohort in a cohort study). Whether a portion is statistically significant can be determined without further ado by the person skilled in the art using various well known statistic evaluation tools, e.g., determination of confidence intervals, p-value determination, Student's t-test, Mann-Whitney test etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001.

It is envisaged in the context of the present invention that the subject suffers from heart failure (HF), in particular from chronic heart failure. Further, the subject may suffer from stabilized acute heart failure.

The term "heart failure" as used herein relates to a diastolic dysfunction or, in particular, of a systolic dysfunction of the heart being accompanied by overt signs of heart failure as known to the person skilled in the art. Preferably, heart failure referred to herein is chronic heart failure (which preferably is caused by systolic dysfunction). Heart failure according to the present invention includes overt and/or advanced heart failure. In overt heart failure, the patient shows symptoms of heart failure as known to the person skilled in the art.

HF can be classified into various degrees of severity.

According to the NYHA (New York Heart Association) classification, heart failure patients are classified as belonging to NYHA classes I, II, III and IV. A patient having heart failure has already experienced structural and functional changes to his pericardium, myocardium, coronary circulation or cardiac valves. He will not be able to fully restore his health, and is in need of a therapeutical treatment. Patients of NYHA Class I have no obvious symptoms of cardiovascular disease but already have objective evidence of functional impairment. Patients of NYHA class II have slight limitation of physical activity. Patients of NYHA class III show a marked limitation of physical activity. Patients of NYHA class IV are unable to carry out any physical activity without discomfort. They show symptoms of cardiac insufficiency at rest.

This functional classification is supplemented by the more recent classification by the American College of Cardiology and the American Heart Association (see J. Am. Coll. Cardiol. 2001; 38; 2101-2113, updated in 2005, see J. Am. Coll. Cardiol. 2005; 46; e1-e82). 4 stages A, B, C and D are defined. Stages A and B are not HF but are considered to help identify patients early before developing "truly" HF. Stages A and B patients are best defined as those with risk factors for the development of HF. For example, patients with coronary artery disease, hypertension, or diabetes mellitus who do not yet demonstrate impaired left ventricular (LV) function, hypertrophy, or geometric chamber distortion would be considered stage A, whereas patients who are asymptomatic but demonstrate LV hypertrophy and/or impaired LV function would be designated as stage B. Stage C then denotes patients with current or past symptoms of HF associated with underlying structural heart disease (the bulk of patients with HF), and stage D designates patients with truly refractory HF.

As used herein, the term "heart failure", in particular, refers to stages B and C of the ACC/AHA classification referred to above. In these stages, the subject shows typical symptoms of heart failure. Accordingly, the patient, preferably, has heart failure classified as stage B or C according to the ACC/AHA classification. Also preferably, the patient has heart failure according to class II or III of the NYHA classification.

Preferably, the heart failure is due to impaired systolic function. Accordingly, it is, in particular, envisaged that the patient suffers from systolic heart failure. Preferably, the patient has a left ventricular ejection fraction (LVEF) of less 50%, more preferably, of less than 45%, and most preferably, of less than 40%.

The patient to be tested on accordance with the method of the present invention shall receive BNP-type peptide guided therapy, i.e. BNP-type peptide guided heart failure therapy. The terms "BNP-type peptide guided therapy" and "BNP-type peptide guided heart failure therapy" are well known in the art. Accordingly, the patient to the tested shall receive heart failure therapy (to be more precise at the time at which the sample is obtained) which is guided by a BNP-type peptide. Thus, it is envisaged that at least one decision as regards to the heart failure therapy for said patient may have been made in the past (and thus prior before obtaining the sample to be tested) based on the level of a BNP-type peptide in said patient, in particular based on the blood, serum or plasma level of a BNP-type peptide in said patient. Accordingly, the patient's level of a BNP-type peptide may have been considered for past decisions on heart failure treatment. Further, it is envisaged that the present decision with respect to heart failure therapy is the first decision which involves the consideration of the level of a BNP-type peptide. Accordingly, the patient who receives BNP-type peptide guided heart failure therapy may be a patient in which BNP-type peptide guided heart failure therapy is initiated (in particular immediately after the sample to be tested has been obtained). Nevertheless, said patient may have received heart failure therapy previously which has not been guided by a BNP-type peptide.

Preferred BNP-type peptides are disclosed elsewhere herein. The BNP-type peptide guided therapy, preferably, may be BNP (Brain natriuretic peptide) guided therapy or, in particular, NT-proBNP (N-terminal pro brain natriuretic peptide) guided therapy (for an explanation of these markers, see elsewhere).

In BNP-type peptide guided therapy, the level of a BNP-type peptide is used for managing heart failure treatment. Based on the level, decisions on the heart failure treatment are made. In principle, a patient with an increased level of a BNP-type peptide receives a more intensified therapy than a patient with a reduced level of this marker. BNP-type peptide guided therapy is well known in the art and is e.g. described by Sanders-van Wijk et al. Eur J Heart Fail (2013) 15 (8): 910-918. Further, BNP-type peptide guided therapies are reviewed by Januzzi, see Archives of Cardiovascular disease (2012), 105, 40 to 50. Both references are herewith incorporated by reference with respect to their entire disclosure content.

In a preferred embodiment, the patient displays a level (in particular a blood, serum or plasma level) of a BNP-type peptide which is below the reference level for said BNP-type peptide being indicative of intensification of heart failure therapy. Accordingly, the patient shall be a patient having a level of a BNP-type peptide which would, when taken alone (i.e. not in combination with the at least one further marker as set forth in step (a) of the aforementioned method, be indicative for a patient who is not eligible to an intensification of heart failure therapy. Preferred reference levels for said BNP-type peptide being indicative of intensification of heart failure therapy to be applied in the context of the present invention are those described in the Examples. Preferred reference levels are within a range from about 80 to 400 pg/ml, or, in particular, from about 80 to 200 pg/ml for BNP, or within a range from about 450 to 2200 pg/ml, or in particular from about 800 pg/ml to 1200 pg/ml for NT-proBNP. Further preferred reference levels are about 100 pg/ml or 400 pg/ml for BNP, and about 1000 pg/ml, or 1200 pg/ml for NT-proBNP. Thus, the patient in accordance with the present invention may display a level of NT-proBNP, in particular a blood, serum or plasma level of NT-proBNP, of less than 1000 pg/ml or 1200 pg/ml.

Further, it is envisaged that the patient who displays a level of a BNP-type which is below the reference level for said BNP-type peptide being indicative of intensification of heart failure therapy has a level (in particular a blood, serum or plasma level) of BNP within the range from about 80 to about 400 pg/ml, in particular within the range of about 80 to about 200 pg/ml. Also, the patient who displays a level of a BNP-type which is below the reference level for said BNP-type peptide being indicative of intensification of heart failure therapy may have a level (in particular a blood, serum or plasma level) of NT-proBNP within the range of 450 to 2200 pg/ml, in particular within the range of 800 to 1200 pg/ml.

Preferably, the term "about" as used herein encompasses a range of + and −20%, more preferably a range of + and −10%, even more preferably a range of + and −5%, and most preferably a range of + and −2%, relative to the specific amount, e.g., indication of a an amount of "about 100" is meant to encompass an amount within a range from 80 to 120. Also, the term "about" refers to the exact amount. Preferably, the levels are measured as described in the Examples.

The term "heart failure therapy" (herein also referred to as "heart failure treatment") as used herein, preferably, refers to any treatment that allows for treating heart failure. Preferably, the term encompasses life style changes, diet regimen, interventions on the body as well as administration of appropriate medicaments, use of devices and/or organ transplants for the treatment of the patient suffering from heart failure.

Life style changes include smoking cessation, reduction of alcohol consumption, increased physical activity, weight loss, sodium (salt) restriction, weight management and healthy eating (such as daily fish oil).

Preferred devices to be applied are pacemakers and resynchronization devices, defibrillator, intra-aortic balloon pumps, and left ventricular assist devices.

In a preferred embodiment, the heart failure therapy is medicinal heart failure therapy. Accordingly, the heart failure therapy preferably encompasses administration of one ore more medicaments. The tem "administering" as used herein is used in the broadest sense and inter alia encompasses oral, enteral, topical administration and "parenteral administration". "Parenteral administration" and "administered parenterally" as used herein mean modes of administration other than enteral and topical administration, usually by injection, and include, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal, epidural, intrasternal injection and infusion. In an embodiment, the medication is administered orally.

Medicaments suitable for the treatment of heart failure are well known in the art, see e.g. Heart Disease, 2008, 8th Edition, Eds. Braunwald, Elsevier Sounders, chapter 24 or the ESC Guidelines for the diagnosis and treatment of acute and chronic heart failure (European Heart Journal (2008) 29, 2388-2442). Preferably, the heart failure treatment includes administration of at least one medicament selected from the group consisting of angiotensin converting enzyme inhibitors (ACE inhibitors), angiotensin II receptor blockers (frequently also referred to as angiotensin II receptor antagonists), beta adrenergic blockers (herein also referred to as beta blockers), diuretics, aldosterone antagonists, adrenergic agonists, positive inotropic agents, calcium antagonists, hydralazine, nitrates, and aspirin. It is particularly preferred that the medicament is an angiotensin converting enzyme inhibitor, an angiotensin II receptor blocker, a beta blocker and/or an aldosterone blocking agent.

Preferred ACE-inhibitors include benazepril, captopril, cilazapril, enalapril, fosinopril, lisinopril, moexipril, perindopril, quinapril, ramipril, spirapril, and trandolapril. A particularly preferred inhibitor is enalapril.

Preferred beta blockers include cebutolol, alprenolol, atenolol, betaxolol, bisoprolol, bupranolol, carazolol, carteolol, carvedilol, celiprolol, metipranolol, metoprolol, nadolol, nebivolol, oxprenolol, penbutolol, pindolol, propanolol, sotalol, tanilolol, and timolol. A particularly preferred beta blocker is atenolol, bisoprolol, carvedilol, or metoprol.

Preferred angiotensin II receptor antagonists are Losartan, Valsartan, Irbesartan, Candesartan, Telmisartan, and Eprosartan. A particularly preferred antagonist is Losartan or Valsartan.

Preferred diuretics are loop diuretics, thiazide and thiazide-like diuretics, K-sparing diuretics, mineralocorticoid receptor antagonists, and vasopres sin antagonists.

Preferred aldosterone antagonists are Eplerone, Spironolactone, Canrenone, Mexrenone, Prorenone; and statines, in particular Atorvastatin, Fluvastatin, Lovastatin, Pravastatin, Rosuvastatin, and Simvastatin. A particularly preferred antagonist is Spironolactone.

Preferred positive inotropic agents are digoxin and digitoxin.

Preferred calcium antagonists are dihydropyridines, verapamil, and diltiazem.

Preferred adrenergic agonists are dobutamine, dopamine, epinephrine, isoprotenerol, nore-pinephrine, and phenylephrine.

The heart failure therapy to be intensified, or not, can be any treatment as set forth herein above. In a preferred embodiment, however, the heart failure therapy comprises administration of at least one medicament as set forth above. In an even more preferred embodiment, the heart failure therapy comprises administration of at least one medicament selected from the group consisting of an angiotensin converting enzyme inhibitor, an angiotensin II receptor blocker, a beta blocker, a diuretic, and an aldosterone antagonist. Most preferably, the heart failure treatment to be intensified comprises the combined administration of a beta blocker and an ACE inhibitor.

In accordance with the method of the present invention, it shall be assessed whether heart failure treatment of the patient to be tested shall be intensified, or not. Preferably, the intensification of heart failure treatment comprises at least one of the following:

increasing the dosage of a previously administered medicament or of previously administered medicaments, the administration of a further or another medicament (or medicaments), in particular the administration of a further medicament (or medicaments) having a different mode of action that the previously administered medicament(s), device therapy, in particular use of pacemaker devices, cardiac resynchronization therapy (CRT), implantable defibrillator devices (ICD) or left ventricular assist devices (LVAD), life style changes, and combinations thereof.

Preferably, the intensification comprises increasing the dosage of a previously administered medicament or of previously administered medicaments, in particular increasing the dosage of a medicament selected from the group consisting of a diuretic, an angiotensin converting enzyme inhibitor, an angiotensin II receptor blocker, an aldosterone antagonist, and a beta blocker. How to increase the dosage, it well known in the art, and, e.g., may be derived from the guidelines. Preferably, the dosing of these medicaments may be increased until the maximally recommended therapeutic dose or until the maximally tolerated dose, whatever is reached first. Also preferably, the dosage may be increased by at least 30% or at least 50%.

Also preferably, the intensification comprises the administration of a further medicament (or medicaments), in particular the administration of a further medicament (or medicaments) having a different mode of action than the previously administered medicaments, or the application of further devices (i.e. of medicaments/devices that were not administered/used prior to carrying out the method of the present invention). Preferred further medicaments include hydralazine, nitrates, inotropic agents, and adrenergic agents. Preferred devices include pacemaker devices, cardiac resynchronization therapy (CRT), and implantable defibrillator devices (ICD).

Also, the intensification of heart failure treatment may further encompass monitoring the patient at short intervals. Accordingly, by carrying out the method of the present invention a patient can be identified who requires closer monitoring, in particular with respect to the heart failure therapy (and, thus, closer observation). With "closer monitoring" it is, preferably, meant that the levels of the markers as referred herein in connection with the method of the present invention are measured in at least one further sample obtained from the patient after a short interval after the sample referred to in step a) of the method of the present invention. Preferred short intervals are mentioned herein below.

A patient who does not require intensification of heart failure treatment, preferably, can continue the heart failure treatment without changing the treatment regimen. Thus, it is not necessary to adapt the dosage of the administered medicament(s) and/or to change the medicaments.

The term "sample" refers to a sample of a body fluid, to a sample of separated cells or to a sample from a tissue or an organ. Samples of body fluids can be obtained by well-known techniques and include, samples of blood, plasma, serum, urine, lymphatic fluid, sputum, ascites, bronchial lavage or any other bodily secretion or derivative thereof. Tissue or organ samples may be obtained from any tissue or organ by, e.g., biopsy. Separated cells may be obtained from the body fluids or the tissues or organs by separating techniques such as centrifugation or cell sorting. E.g., cell-, tissue- or organ samples may be obtained from those cells, tissues or organs which express or produce the biomarker. The sample may be frozen, fresh, fixed (e.g. formalin fixed), centrifuged, and/or embedded (e.g. paraffin embedded), etc. The cell sample can, of course, be subjected to a variety of well-known post-collection preparative and storage techniques (e.g., nucleic acid and/or protein extraction, fixation, storage, freezing, ultrafiltration, concentration, evaporation, centrifugation, etc.) prior to assessing the amount of the marker in the sample. Likewise, biopsies may also be subjected to post-collection preparative and storage techniques, e.g., fixation.

In an embodiment the sample is a blood, serum or, in particular, a plasma sample.

The sample may be obtained from the patient in increasing order of preference at least one month, at least six months, or at least 12 months after initiation of heart failure therapy, in particular of BNP-type peptide guided therapy. Preferably, said therapy is medicinal heart failure therapy.

The level of the biomarkers as referred to herein can be determined in the same sample or in different samples (i.e. in two or three different samples) from the patient.

The term "measuring" the level of a marker as referred to herein refers to the quantification of the biomarker, e.g. to determining the level of the biomarker in the sample, employing appropriate methods of detection described elsewhere herein. In an embodiment, the level of the at least one biomarker is measured by contacting the sample with a detection agent that specifically binds to the respective marker, thereby forming a complex between the agent and said marker, detecting the level of complex formed, and thereby measuring the level of said marker. If the biomarker is uric acid, the level of said biomarker may be measured by contacting the sample with detection agent, in particular an enzyme or compound, that allows for the conversion of said biomarker, e.g. that allows for the oxidation of uric acid. The enzyme may be an uricase (EC 1.7.3.3) which catalyzes the oxidation of uric acid to 5-hydroxyisourate. Also, the enzyme can be a peroxidase. The compound may be phosphotungstic acid. If the marker is urea, the detection agent may be urease. If the marker is glucose, the detection agent may be a hexokinase. If the marker is creatinine, the detection agent may be picric acid (which forms a complex with creatinine). The level of the complex of picric acid and creatinine may be measured.

The term "Growth-Differentiation Factor-15" or "GDF-15" relates to a polypeptide being a member of the transforming growth factor (TGF) cytokine superfamily. The terms polypeptide, peptide and protein are used interchangeable throughout this specification. GDF-15 was originally cloned as macrophage-inhibitory cytokine 1 and later also identified as placental transforming growth factor-15, placental bone morphogenetic protein, non-steroidal anti-inflammatory drug-activated gene 1, and prostate-derived factor (Bootcov loc cit; Hromas, 1997 Biochim Biophys Acta 1354:40-44; Lawton 1997, Gene 203:17-26; Yokoyama-Kobayashi 1997, J Biochem (Tokyo), 122:622-626; Paralkar 1998, J Biol Chem 273:13760-13767). Similar to other TGF-related cytokines, GDF-15 is synthesized as an inactive precursor protein, which undergoes disulfide-linked homodimerization. Upon proteolytic cleavage of the N terminal pro-peptide, GDF-15 is secreted as a ~28 kDa dimeric protein (Bauskin 2000, Embo J 19:2212-2220). Amino acid sequences for GDF-15 are disclosed in WO99/06445, WO00/70051, WO2005/113585, Bottner 1999, Gene 237: 105-111, Bootcov loc. cit, Tan loc. cit., Baek 2001, Mol Pharmacol 59: 901-908, Hromas loc cit, Paralkar loc cit, Morrish 1996, Placenta 17:431-441 or Yokoyama-Kobayashi loc cit. GDF-15 as used herein encompasses also variants of the aforementioned specific GDF-15 polypeptides. Such variants have at least the same essential biological and immunological properties as the specific GDF-15 polypeptides. In particular, they share the same essential biological and immunological properties if they are detectable by the same specific assays referred to in this specification, e.g., by ELISA assays using polyclonal or monoclonal antibodies specifically recognizing the said GDF-15 polypeptides. A preferred assay is described in the accompanying Examples. Moreover, it is to be understood that a variant as referred to in accordance with the present invention shall have an amino acid sequence which differs due to at least one amino acid substitution, deletion and/or addition wherein the amino acid sequence of the variant is still, preferably, at least about 50%, at least about 60%, at least about 70%, at least about 80%, at least about 85%, at least about 90%, at least about 92%, at least about 95%, at least about 97%, at least about 98%, or at least about 99% identical with the amino sequence of the specific GDF-15 polypeptides, preferably with the amino acid sequence of human GDF-15, more preferably over the entire length of the specific GDF-15, e.g. of human GDF-15. The degree of identity between two amino acid sequences can be determined as described above. Variants referred to above may be allelic variants or any other species specific homologs, paralogs, or orthologs. Moreover, the variants referred to herein include fragments of the specific GDF-15 polypeptides or the aforementioned types of variants as long as these fragments have the essential immunological and biological properties as referred to above. Such fragments may be, e.g., degradation products of the GDF-15 polypeptides. Further included are variants which differ due to posttranslational modifications such as phosphorylation or myristylation.

The Insulin like growth factor binding protein (IGFBP) system plays an important role in cell growth and differentiation. It comprises two ligands, IGF-I and IGF-II, two receptors, type 1 and type 2 IGF receptors, and as of 1995 six IGF-binding proteins (IGFBPs), IGFBP-1 to -6 (Jones, J. I., et al., Endocr. Rev. 16 (1995) 3-34). Recently the IGFBP family has been expanded to include the IGFBP-related proteins (IGFBP-rPs), which have significant structural similarities with the IGFBPs (Hwa, V., et al., Endocr. Rev 20 (1999) 761-787). Thus, the IGFBP superfamily includes the six conventional IGFBPs, which have high affinity for IGFs, and at least 10 IGFBP-rPs, which not only share the conserved amino-terminal domain of the IGFBPs but also show some degree of affinity for IGFs and insulin. The IGFBP-rPs are a group of cysteine-rich proteins that control diverse cellular functions, such as cellular growth, cell adhesion and migration, and synthesis of the extracellular matrix. In addition, these proteins might be involved in biological processes like tissue proliferation and differentiation, reproduction, angiogenesis, wound repair, inflammation, fibrosis, and tumorigenesis (Hwa, V., et al., Endocr. Rev 20 (1999) 761-787).

IGF binding protein 7 (=IGFBP7) is a 30-kDa modular glycoprotein known to be secreted by endothelial cells, vascular smooth muscle cells, fibroblasts, and epithelial cells (Ono, Y., et al., Biochem Biophys Res Comm 202 (1994) 1490-1496). In the literature this molecule has also been denominated as FSTL2; IBP 7; IGF binding protein related protein I; IGFBP 7; IGFBP 7v; IGFBP rP1; IGFBP7; IGFB-PRP1; insulin like growth factor binding protein 7; insulin like growth factor binding protein 7 precursor; MAC25; MAC25 protein; PGI2 stimulating factor; and PSF or Prostacyclin stimulating factor. Northern blot studies revealed a wide expression of this gene in human tissues, including heart, brain, placenta, liver, skeletal muscle, and pancreas (Oh, Y., et al., J. Biol. Chem. 271 (1996) 30322-30325).

IGFBP7 was initially identified as a gene differentially expressed in normal leptomeningeal and mammary epithelial cells, compared with their counterpart tumor cells, and named meningioma-associated cDNA (MAC25) (Burger, A. M., et al., Oncogene 16 (1998) 2459-2467). The expressed protein was independently purified as a tumor derived adhesion factor (later renamed angiomodulin) (Sprenger, C. C., et al., Cancer Res 59 (1999) 2370-2375) and as a prostacyclin stimulating factor (Akaogi, K., et al., Proc Natl Acad Sci USA 93 (1996) 8384-8389). It has additionally been reported as T1A12, a gene down-regulated in breast carcinomas (StCroix, B., et al., Science 289 (2000) 1197-1202).

Differential expression of IGFBP7 mRNA was measured in patients suffering from various diseases including cardiac disease, kidney disease, inflammatory diseases (U.S. Pat. No. 6,709,855 to Scios Inc.) and vascular graft disease (US 2006/0,003,338).

A number of different assays has been described and used to test for the hormone binding properties of IGFBP7. Low affinity IGF binding was analyzed via competitive affinity cross-linking assays. Recombinant human mac25 protein specifically binds IGF-I and -II (Oh, Y., et al., J. Biol. Chem. 271 (1996) 20322-20325; Kim, H. S., et al., Proc. Natl. Acad. Sci USA 94 (1997) 12981-12986.) IGFBP activity can also be detected by measuring the ability of the protein to bind radiolabeled IGF in Western ligand blotting.

Preferably, the term "IGFBP7" refers to human IGFBP7. The sequence of the protein is well known in the art and is e.g. accessible via GenBank (NP_001240764.1). IGFBP7 as used herein, preferably, encompasses also variants of the specific IGFBP7 polypeptides. For an explanation of the term "variants", please see above.

Immunological determination of circulating IGFBP7 was performed recently. Low levels of this analyte were detected in random human sera and increased serum levels have been seen in association with insulin-resistance (Lopez-Bermejo, A., et al., J. Clinical Endocrinology and Metabolism 88 (2003) 3401-3408, Lopez-Bermejo, A., et al., Diabetes 55 (2006) 2333-2339).

The marker Endostatin is well known in the art. Endostatin was originally isolated from murine hemangioendothelioma as a 20 kDA proteolytic fragment of type XVIII collagen (O'Reilly, M. S. et al., Cell 88 (1997) 277-285). Collagens represent a family of extracellular matrix proteins with a characteristic triple-helical conformation forming supra-molecular aggregates that play a dominant role in maintaining tissue structural integrity. Excessive collagen deposition leads to fibrosis disrupting the normal functioning of surrounding tissues. Collagen XVIII is a member of the Multiplexin family of collagens with multiple interruptions in the central triple-helical domain and a unique non-triple-helical domain at the C-terminus mainly in basement membranes. The sequence of the short isoform of human type alpha 1-chain of collagen XVIII (SwissProt: P39060) is e.g. disclosed in WO2010/124821 which herewith is incorporated by reference with respect to its entire disclosure content.

Endostatin is released from the alpha 1 chain of collagen XVIII by action of various proteolytic enzymes (for details see Ortega, N. and Werb, Z., Journal of Cell Science 115 (2002) 4201-4214—the full disclosure of this paper is herewith incorporated by reference). Endostatin as used herein is represented by the collagen XVIII fragment spanning from amino acid position 1337 to amino acid position 1519 of collagen XVIII as disclosed in WO2010/124821. The hinge region at the C-terminus of the alpha chain of collagen XVIII contains several protease sensitive sites and a number of enzymes, including neutrophil elastase, cathepsins and matrix metalloproteinases are known to generate endostatin by cleaving the collagen chain in this region. These proteases do not exclusively release endostatin but also may release other, larger fragments that contain the endostatin sequence. As obvious to the skilled artisan such larger fragments will also be measured by an immunoassay for endostatin.

Osteopontin (OPN), also known as bone sialoprotein I (BSP-1 or BNSP), early T-lymphocyte activation (ETA-1), secreted phosphoprotein 1 (SPP1), 2ar and *Rickettsia* resistance (Ric), is a polypeptide which is a highly negatively charged, extracellular matrix protein that lacks an extensive secondary structure. It is composed of about 300 amino acids (297 in mouse; 314 in human) and is expressed as a 33-kDa nascent protein; there are also functionally important cleavage sites. OPN can go through posttranslational modifications which increase its apparent molecular weight to about 44 kDa. The sequence of osteopontin is well known in the art (human osteopontin: UniProt P10451, GenBank NP_000573.1) Osteopontin is found in normal plasma, urine, milk and bile (U.S. Pat. Nos. 6,414,219; 5,695,761; Denhardt, D. T. and Guo, X., FASEB J. 7 (1993) 1475-1482; Oldberg, A., et al., PNAS 83 (1986) 8819-8823; Oldberg, A., et al., J. Biol. Chem. 263 (1988) 19433-19436; Giachelli, C M., et al., Trends Cardiovasc. Med. 5 (1995) 88-95). The human OPN protein and cDNA have been isolated and sequenced (Kiefer M. C, et al., Nucl. Acids Res. 17 (1989) 3306). OPN functions in cell adhesion, chemotaxis, macrophage-directed interleukin-10. OPN is known to interact with a number of integrin receptors. Increased OPN expression has been reported in a number of human cancers, and its cognate receptors (av-b3, av-b5, and av-b1 integrins and CD44) have been identified. In vitro studies by Irby, R. B., et al., Clin. Exp. Metastasis 21 (2004) 515-523 indicate that both endogenous OPN expression (via stable transfection) as well as exogenous OPN (added to culture medium) enhanced the motility and invasive capacity of human colon cancer cells in vitro.

Endostatin is a potent inhibitor of angiogenesis and blood vessel growth. The relationship between endostatin and cytokine networks is undetermined, but it is known that endostatin is able to alter expression of a wide range of genes (Abdollahi, A. et al., Mol. Cell 13 (2004) 649-663).

Endostatin as used herein, preferably, encompasses also variants of the specific endostatin polypeptides. For an explanation of the term "variants", please see above.

Mimecan is a small proteoglycan with leucin-rich repeats and a precursor comprising 298 amino acids. Other names of mimecan are OGN, osteoglycin, OG, OIF, SLRR3A.

Mimecan is a member of the secreted small leucine rich proteoglycans (SLRP) family with structurally related core proteins. The common feature shared by all SLRPs is the tandem leucine-rich repeat (LRR) units in the C-terminal half of the core protein. In the N-terminal region, however, each class of SLRP has a unique domain containing a cysteine cluster with conserved spacing called the LRR N-domain. Class III SLRPs contain six carboxyl LRRs and include mimecan, epiphycan and opticin.

Functional studies from mouse knockouts for class I and II members, such as decorin, biglycan, lumecan and fibromodulin, showed that the SLRP-deficient mice displayed a wide array of defects attributable to abnormal collagen fibrillogenesis suggesting that these SLRPs play important roles in establishing and maintaining the collagen matrix (Ameye, L. and Young, M. F., Glycobiology 12 (2002) 107R-116R). Deficiency of class III mimecan also caused collagen fibril abnormalities (Tasheva, E. S. et al., Mol. Vis. 8 (2002) 407-415).

Mimecan is a multifunctional component of the extracellular matrix. It binds to a variety of other proteins (IGF2, IKBKG, IFNB1, INSR, CHUK, IKBKB, NFKBIA, IL1 5, Cd3, retinoic acid, APP, TNF, lipopolysaccharide, c-ab1 oncogene 1, receptor tyrosine kinase, v-src sarcoma viral oncogene). These diverse binding activities may account for the ability of mimecan to exert diverse functions in many tissues.

Mimecan has been found in cornea, bone, skin and further tissues. Its expression pattern is altered in different pathological conditions. Despite the increasing amount of data on the biological role of mimecan its function is still not clear. Mimecan has been shown to be involved in regulating collagen fibrillogenesis, a process essential in development, tissue repair, and metastasis (Tasheva et al., Mol. Vis. 8 (2002) 407-415). It plays a role in bone formation in conjunction with TGF-beta-1 or TGF-beta-2.

The sequence of the human mimecan polypeptide is well known in the art and may be assessed, e.g., via GenBank accession number NP_054776.1 GI:7661704. Further, the sequence is disclosed in WO2011/012268. Mimecan as used herein, preferably, encompasses also variants of the specific mimecan polypeptides. For an explanation of the term "variants", please see above. In context of the present invention, mimecan is preferably determined as described in WO2011/012268.

The term "soluble Flt-1" or "sFlt-1" as used herein refers to polypeptide which is a soluble form of the VEGF receptor Flt1. It was identified in conditioned culture medium of human umbilical vein endothelial cells. The endogenous soluble Flt1 (sFlt1) receptor is chromatographically and immunologically similar to recombinant human sFlt1 and binds [125I] VEGF with a comparable high affinity. Human sFlt1 is shown to form a VEGF-stabilized complex with the extracellular domain of KDR/Flk-1 in vitro. Preferably, sFlt1 refers to human sFlt1. More preferably, human sFlt1 can be deduced from the amino acid sequence of Flt-1 as shown in Genbank accession number P17948, GI: 125361. An amino acid sequence for mouse sFlt1 is shown in Genbank accession number BAA24499.1, GI: 2809071.

The term "sFlt-1" used herein also encompasses variants of the aforementioned specific sFlt-1 polypeptide. Such variants have at least the same essential biological and immunological properties as the specific sFlt-1 polypeptide. In particular, they share the same essential biological and immunological properties if they are detectable by the same specific assays referred to in this specification, e.g., by ELISA assays using polyclonal or monoclonal antibodies specifically recognizing the said sFlt-1 polypeptide. For a more detailed explanation of the term "variants", please see above.

Galectin-3 (Gal-3) is a structurally unique member of a family of beta-galactoside-binding lectins. Expression of galectin-3 has been associated with the epithelium and inflammatory cells including macrophages, neutrophils and mast cells. Galectin-3 has been implicated in a variety of biological processes important in heart failure including myofibroblast proliferation, fibrogenesis, tissue repair, cardiac remodeling and inflammation. Galectin-3 is approximately 30 kDa and, like all galectins, contains a carbohydrate-recognition-binding domain (CRD) of about 130 amino acids that enable the specific binding of β-galactosides. Galectin-3 is encoded by a single gene, LGALS3. It comprises an N-terminal domain with tandem repeats of short amino acid segments (a total of 110-130 amino acids) linked to a single C-terminal CRD of about 130 amino acids. It is expressed in the nucleus, cytoplasm, mitochondrion, cell surface, and extracellular space—This protein has been shown to be involved in the following biological processes: cell adhesion, cell activation and chemoattraction, cell growth and differentiation, cell cycle, and apoptosis. Elevated levels of galectin-3 have been found to be significantly associated with higher risk of death in both acute decompensated heart failure and chronic heart failure populations (see, e.g., DeFilippi C, Christenson R, Shah R, et al. (2009). Clinical validation of a novel assay for galectin-3 for risk assessment in acutely destabilized heart failure.)

The protein sequence of Galectin-3 is well known in the art, see e.g. uniprot accession number P17931 (version 5, Nov. 25, 2008), GenBank accession number NP_002297.2 NM_002306.3.

ST2 is a member of the IL-1 receptor family that is produced by cardiac fibroblasts and cardiomyocytes under conditions of mechanical stress. ST2 is an interleukin-1 receptor family member and exists in both membrane-bound isoform and a soluble isoform (sST2). In the context of the present invention, the amount of soluble ST2 shall be determined (see Dieplinger et al. (Clinical Biochemistry, 43, 2010: 1169 to 1170). ST2 also known as Interleukin 1 receptor-like 1 or IL1RL1, is encoded in humans by the IL1RL1 gene. The sequence of the human ST2 polypeptide is well known in the art, and e.g. accessible via GenBank, see NP_003847.2 GI:27894328. Soluble ST2 (sST2) is believed to function as a decoy receptor by binding IL-33 and abrogating the otherwise cardioprotective effect of IL-33 signaling through the cell membrane-bound form of ST2.

CRP, herein also referred to as C-reactive protein, is an acute phase protein that was discovered more than 75 years ago to be a blood protein that binds to the C-polysaccharide of pneumococci. CRP is known as a reactive inflammatory marker and is produced by a distal organ (i.e. the liver) in response or reaction to chemokines or interleukins originating from the primary lesion site. CRP consists of five single subunits, which are non covalently linked and assembled as a cyclic pentamer with a molecular weight of approximately 110-140 kDa. Preferably, CRP as used herein relates to human CRP. The sequence of human CRP is well known and disclosed, e.g., by Woo et al. (J. Biol. Chem. 1985. 260 (24), 13384-13388). The level of CRP is usually low in normal individuals but can rise 100- to 200-fold or higher due to inflammation, infection or injury (Yeh (2004) Circulation. 2004; 109:II-11-II-14). It is known that CRP is an independent factor for the prediction of a cardiovascular risk. Particularly, it has been shown that CRP is suitable as a predictor for myocardial infarction, stroke, peripheral arterial disease and sudden cardiac death. Moreover, elevated CRP amounts may also predict recurrent ischemia and death in patients with acute coronary syndrome (ACS) and those undergoing coronary intervention. Determination of CRP is recommended by expert panels (e.g. by the American Heart Association) in patients with a risk of coronary heart disease (see also Pearson et al. (2003) Markers of Inflammation and Cardiovascular Disease. Circulation, 107: 499-511). The term CRP also relates to variants thereof.

Preferably, the amount of CRP in a sample of a patient is determined by using CRP assays with a high sensitivity. The CRP determined by such assays is frequently also referred to as high sensitivity CRP (hsCRP). hsCRP assays are, e.g., used to predict the risk of heart disease. Suitable hsCRP assays are known in the art. A particularly preferred hsCRP assay in the context of the present invention is the Roche/Hitachi CRP (Latex) HS test with a detection limit of 0.1 mg/l.

Interleukin-6 (abbreviated as IL-6) is an interleukin is secreted by T cells and macrophages to stimulate immune response, e.g. during infection and after trauma, especially burns or other tissue damage leading to inflammation. It acts as both a pro-inflammatory and anti-inflammatory cytokine. In humans, it is encoded by the IL6 gene. The sequence of human IL-6 can be assessed via GenBank (see NM_000600.3 for the polynucleotide sequence, and NP_000591.1 for the amino acid sequence). IL-6 signals through a cell-surface type I cytokine receptor complex consisting of the ligand-binding IL-6Rα chain (CD126), and the signal-transducing component gp130 (also called CD130). CD130 is the common signal transducer for several cytokines including leukemia inhibitory factor (LIF), ciliary neurotropic factor, oncostatin M, IL-11 and cardiotrophin-1, and is almost ubiquitously expressed in most tissues. In contrast, the expression of CD126 is restricted to certain tissues. As IL-6 interacts with its receptor, it triggers the gp130 and IL-6R proteins to form a complex, thus activating the receptor. These complexes bring together the intracellular regions of gp130 to initiate a signal transduction cascade through certain transcription factors, Janus kinases (JAKs) and Signal Transducers and Activators of Transcription.

The marker Cystatin C is well known in the art. Cystatin C is encoded by the CST3 gene and is produced by all nucleated cells at a constant rate and the production rate in humans is remarkably constant over the entire lifetime. Elimination from the circulation is almost entirely via glomerular filtration. For this reason the serum concentration of cystatin C is independent from muscle mass and gender in the age range 1 to 50 years. Therefore cystatin C in plasma and serum has been proposed as a more sensitive marker for GFR. The sequence of the human Cystatin C polypeptide can be assessed via Genbank (see e.g. accession number NP_000090.1). The biomarker can be determined by particle enhanced immunoturbidimetric assay. Human cystatin C agglutinates with latex particles coated with anti-cystatin C antibodies. The aggregate is determined turbidimetrically.

The marker Prealbumin is well known by the skilled person. It is a tryptophan-rich protein which is synthesized in hepatocytes and has a molar mass of 55000 daltons. At a pH of 8.6, an electrophoretic band appears prior to albumin in a relative amount of <2.5% due to its greater rate of diffusion to the anode. Its function is to bind and transport low molecular weight retinol-binding proteins (molar mass of less than 21000 daltons), preventing their glomerular filtration. 30-50% of circulating prealbumin is complexed by retinol-binding protein. Furthermore, it binds and transports thyroxine (T4), nevertheless its affinity to this hormone is less than that of thyroxine-binding globulin. The sequence of the human Prealbumin polypeptide can be assessed via Genbank (see e.g. accession number NP_000362.1). Various methods are available for the determination of prealbumin, such as radial immunodiffusion (RID), nephelometry and turbidimetry.

The marker "creatinine" is well known in the art. In muscle metabolism, creatinine is synthesized endogenously from creatine and creatine phosphate. Under conditions of normal renal function, creatinine is excreted by glomerular filtration. Creatinine determinations are performed for the diagnosis and monitoring of acute and chronic renal disease as well as for the monitoring of renal dialysis. Creatinine concentrations in urine can be used as reference values for the excretion of certain analytes (albumin, α-amylase). Creatinine can be determined as described by Popper et al., (Popper H et al. Biochem Z 1937; 291:354), Seelig and Wüst (Seelig H P, Wüst H. Ärztl Labor 1969; 15:34) or Bartels (Bartels H et al. Clin Chim Acta 1972; 37:193). For example, sodium hydroxide and picric acid are added to the sample to start the formation of creatinine-picric acid complex. In alkaline solution, creatinine forms a yellow-orange complex with picrate. The color intensity is directly proportional to the creatinine concentration and can be measured photometrically.

Uric acid is the final product of purine metabolism in a subject organism. The IUPAC name is 7,9-dihydro-3H-purine-2,6,8-trione. The compound is frequently also referred to as urate, Lithic acid, 2,6,8-trioxypurine, 2,6,8-trihydroxypurine, 2,6,8-Trioxopurine, 1H-Purine-2,6,8-triol (compound formula $C_5H_4N_4O_3$, PubChem CID 1175, CAS number 69-93-2).

Uric acid measurements are used in the diagnosis and treatment of numerous renal and metabolic disorders, including renal failure, gout, leukemia, psoriasis, starvation or other wasting conditions, and of patients receiving cytotoxic drugs. The oxidation of uric acid provides the basis for two approaches to the quantitative determination of this purine metabolite. One approach is the reduction of phosphotungstic acid in an alkaline solution to tungsten blue, which is measured photometrically. A second approach, described by Praetorius and Poulson, utilizes the enzyme uricase to oxidize uric acid; this method eliminates the interferences intrinsic to chemical oxidation (Praetorius E, Poulsen H. Enzymatic Determination of Uric Acid with Detailed Directions. Scandinav J Clin Lab Investigation 1953; 3:273-280). Uricase can be employed in methods that involve the UV measurement of the consumption of uric acid or in combination with other enzymes to provide a colorimetric assay. Another method is the colorimetric method developed by Town et al. (Town M H, Gehm S, Hammer B, Ziegenhorn J. J Clin Chem Clin Biochem 1985; 23:591). The sample is initially incubated with a reagent mixture containing ascorbate oxidase and a clearing system. In this test system it is important that any ascorbic acid present in the sample is eliminated in the preliminary reaction; this precludes any ascorbic acid interference with the subsequent POD indicator reaction. Upon addition of the starter reagent, oxidation of uric acid by uricase begins.

In the context of the present invention, uric acid can be determined by any method deemed appropriate. Preferably, the biomarker is determined by the aforementioned methods. More preferably, uric acid is determined by applying a slight modification of the colorimetric method described above. In this reaction, the peroxide reacts in the presence of peroxidase (POD), N-ethyl-N-(2-hydroxy-3-sulfopropyl)-3-methylaniline (TOOS), and 4-aminophenazone to form a quinone-diimine dye. The intensity of the red color formed is proportional to the uric acid concentration and is determined photometrically.

Urea is the major end product of protein nitrogen metabolism. It has the chemical formula $CO(NH_2)_2$ and is synthesized by the urea cycle in the liver from ammonia which is produced by amino acid deamination. Urea is excreted mostly by the kidneys but minimal amounts are also excreted in sweat and degraded in the intestines by bacterial action. Determination of blood urea nitrogen is the most widely used screening test for renal function. Urea can be measured by an in vitro test for the quantitative determination of urea/urea nitrogen in human serum, plasma and urine on Roche/Hitachi cobas c systems. The test can be carried out automatically using different analysers including cobas c 311 and cobas c 501/502. The assay is a kinetic assay with urease and glutamate dehydrogenase. Urea is hydrolyzed by urease to form ammonium and carbonate. In the second reaction 2-oxoglutarate reacts with ammonium in the presence of glutamate dehydrogenase (GLDH) and the coenzyme NADH to produce L-glutamate. In this reaction 2 moles of NADH are oxidized to $NAD^+$ for each mole of urea hydrolyzed. The rate of decrease in the NADH concentration is directly proportional to the urea concentration in the specimen and is measured photometrically.

The marker Glucose is well known in the art as well. As used herein, the marker preferably refers to D-Glucose. The level of the marker can be determined by well known methods. For example, the marker can be phosphorylated to D-glucose-6-phosphate in the presence of the enzyme hexokinase (HK) and adenosine-5'-triphosphate (ATP) with the simultaneous formation of adenosine-5'-diphosphate (ATP). In the present of the enzyme glucose-6-phosphate dehydrogenase, D-glucose-6-phosphate is oxidized to by NADP to D-gluconate phosphate with the formation of reduced nicotinamide-adenine dinucleotide phosphate (NADPH). The amount of NADPH formed in this reaction is stoichiometric to the amount of D-glucose. NADPH can be measured by means of light absorbance.

The marker Sodium is well known in the art. Sodium is the major extracellular cation and functions to maintain fluid distribution and osmotic pressure. Some causes of decreased levels of sodium include prolonged vomiting or diarrhea, diminished reabsorption in the kidney and excessive fluid retention. Common causes of increased sodium include excessive fluid loss, high salt intake and increased kidney reabsorption. The level of the marker can be determined by applying an Ion Selective Electrode (ISE) which makes use of the unique properties of certain membrane materials to develop an electrical potential (electromotive force, EMF) for the measurements of ions in solution. The electrode has a selective membrane in contact with both the test solution and an internal filling solution. The internal filling solution contains the test ion at a fixed concentration. Because of the particular nature of the membrane, the test ions will closely associate with the membrane on each side. The membrane EMF is determined by the difference in concentration of the test ion in the test solution and the internal filling solution. The EMF develops according to a Nernst equation for a specific ion in solution.

The marker Hemoglobin (Hb) is well known in the art. Hemoglobin comprises four protein subunits, each containing a heme moiety, and is the red-pigmented protein located in the erythrocytes. Its main function is to transport oxygen and carbon dioxide in blood. Each Hb molecule is able to bind four oxygen molecules. Hb consists of a variety of subfractions and derivatives. The term "hemoglobin" as used herein, preferably, refers to total hemoglobin. The level of Hemoglobin can be measured by well known methods, e.g. by oxidation of hemoglobin to methemoglobin by potassium hexacyanoferrate (III) ($Fe^{2+} \rightarrow Fe^{3+}$). The hemoglobin level is proportional to the color intensity and, e.g., can be measured at a wavelength of 567 nm and 37° C. The level of hemoglobin can be also measured by contacting the sample with an antibody which specifically binds to hemoglobin.

The marker HbA1c (glycated hemoglobin, Glycohemoglobin) is well known in the art as well. HbA1c is one of the glycated hemoglobins, a subfraction formed by the attachment of various sugars to the Hb molecule. HbA1c is formed in two steps by the nonenzymatic reaction of glucose with the N-terminal amino group of the β-chain of normal adult Hb (HbA). The first step is reversible and yields labile HbA1c. This is rearranged to form stable HbA1c in a second reaction step. In the erythrocytes, the relative amount of HbA converted to stable HbA1c increases with the average concentration of glucose in the blood. The conversion to stable HbA1c is limited by the erythrocyte's life span of approximately 100 to 120 days. The level of Hemoglobin can be measured by well known methods. Preferably, the measurement of the level of HbA1c encompasses the measurement of the level of all hemoglobin variants which are glycated at the β-chain N-terminus of HbA (adult hemoglobin). In an embodiment the level of this marker is measured by contacting the sample with an antibody which specifically binds to this marker. In this case, Clycohemoglobin (HbA1c) in the sample reacts with anti-HbA1c antibody to form soluble antigen-antibody complexes Hematocrit (Ht or HCT) also known as packed cell volume (PCV) or erythrocyte volume fraction (EVF), is the volume percentage (%) of red blood cells in blood. As used, the term "hematocrit", preferably, refers to the percentage of packed red blood cells in a volume of whole blood. Hematocrit can be determined by centrifuging heparinized blood in a capillary tube (also known as a microhematocrit tube) at 10,000 RPM for five minutes. This separates the blood into layers. The volume of packed red blood cells divided by the total volume of the blood sample gives the PCV. Because a tube is used, this can be calculated by measuring the lengths of the layers. With modern lab equipment, the hematocrit is calculated by an automated analyzer and not directly measured. It is determined by multiplying the red cell count by the mean cell volume. The hematocrit is slightly more accurate as the PCV includes small amounts of blood plasma trapped between the red cells. An estimated hematocrit as a percentage may be derived by tripling the hemoglobin concentration in g/dL and dropping the units.

The term "QRS duration" is well known in the art. The QRS duration is a standard measure in medicine and describes the duration of the QRS group on the surface electrocardiogram (ECG) that is indication the duration of electrical excitation of the ventricles. Preferably, the QRS duration is measured by an ECG device.

The biomarkers as referred to herein can be detected using methods generally known in the art. Methods of detection generally encompass methods to quantify the level of a biomarker in the sample (quantitative method). It is generally known to the skilled artisan which of the following methods are suitable for qualitative and/or for quantitative detection of a biomarker. Samples can be conveniently assayed for, e.g., proteins using Westerns and immunoassays, like ELISAs, RIAs, fluorescence-based immunoassays, which are commercially available. Further suitable methods to detect biomarker include measuring a physical or chemical property specific for the peptide or polypeptide such as its precise molecular mass or NMR spectrum. Said methods comprise, e.g., biosensors, optical devices coupled to immunoassays, biochips, analytical devices such as mass-spectrometers, NMR-analyzers, or chromatography devices. Further, methods include microplate ELISA-based methods, fully-automated or robotic immunoassays (available for example on Elecsys™ analyzers), CBA (an enzymatic Cobalt Binding Assay, available for example on Roche-Hitachi™ analyzers), and latex agglutination assays (available for example on Roche-Hitachi™ analyzers).

For the detection of biomarker proteins as referred to herein a wide range of immunoassay techniques using such an assay format are available, see, e.g., U.S. Pat. Nos. 4,016,043, 4,424,279, and 4,018,653. These include both single-site and two-site or "sandwich" assays of the non-competitive types, as well as in the traditional competitive binding assays. These assays also include direct binding of a labeled antibody to a target biomarker.

Sandwich assays are among the most useful and commonly used immunoassays.

Methods for measuring electrochemiluminescent phenomena are well-known. Such methods make use of the ability of special metal complexes to achieve, by means of oxidation, an excited state from which they decay to ground state, emitting electrochemiluminescence. For review see Richter, M. M., Chem. Rev. 104 (2004) 3003-3036.

Biomarkers can also be detected by generally known methods including magnetic resonance spectroscopy (NMR spectroscopy), Gas chromatography-mass spectrometry (GC-MS), Liquid chromatography-mass spectrometry (LC-MS), High and ultra-HPLC HPLC such as reverse phase HPLC, for example, ion-pairing HPLC with dual UV-wavelength detection, capillary electrophoresis with laser-induced fluorescence detection, anion exchange chromatography and fluorescent detection, thin layer chromatography.

Preferably, measuring the level of a biomarker as referred to herein comprises the steps of (a) contacting a cell capable of eliciting a cellular response the intensity of which is indicative of the level of the peptide or polypeptide with the said peptide or polypeptide for an adequate period of time, (b) measuring the cellular response. For measuring cellular responses, the sample or processed sample is, preferably, added to a cell culture and an internal or external cellular response is measured. The cellular response may include the measurable expression of a reporter gene or the secretion of a substance, e.g. a peptide, polypeptide, or a small molecule. The expression or substance shall generate an intensity signal which correlates to the level of the peptide or polypeptide.

Also preferably, measuring the level of a peptide or polypeptide comprises the step of measuring a specific intensity signal obtainable from the peptide or polypeptide in the sample. As described above, such a signal may be the signal intensity observed at an m/z variable specific for the peptide or polypeptide observed in mass spectra or a NMR spectrum specific for the peptide or polypeptide.

Measuring the level of a peptide or polypeptide may, preferably, comprises the steps of (a) contacting the peptide with a specific binding agent, (b) (optionally) removing non-bound binding agent, (c) measuring the level of bound binding agent, i.e. the complex of the binding agent formed in step (a). According to a preferred embodiment, said steps of contacting, removing and measuring may be performed by an analyzer unit of the system disclosed herein. According to some embodiments, said steps may be performed by a single analyzer unit of said system or by more than one analyzer unit in operable communication with each other. For example, according to a specific embodiment, said system disclosed herein may include a first analyzer unit for performing said steps of contacting and removing and a second analyzer unit, operably connected to said first analyzer unit by a transport unit (for example, a robotic arm), which performs said step of measuring.

The bound binding agent, i.e. the binding agent or the binding agent/peptide complex, will generate an intensity signal. Binding according to the present invention includes both covalent and non-covalent binding. A binding agent according to the present invention can be any compound, e.g., a peptide, polypeptide, nucleic acid, or small molecule, binding to the peptide or polypeptide described herein. Preferred binding agents include antibodies, nucleic acids, peptides or polypeptides such as receptors or binding partners for the peptide or polypeptide and fragments thereof comprising the binding domains for the peptides, and aptamers, e.g. nucleic acid or peptide aptamers. Methods to prepare such binding agents are well-known in the art. For example, identification and production of suitable antibodies or aptamers is also offered by commercial suppliers. The person skilled in the art is familiar with methods to develop derivatives of such binding agents with higher affinity or specificity. For example, random mutations can be introduced into the nucleic acids, peptides or polypeptides. These derivatives can then be tested for binding according to screening procedures known in the art, e.g. phage display. Antibodies as referred to herein include both polyclonal and monoclonal antibodies, as well as fragments thereof, such as Fv, Fab and F(ab)2 fragments that are capable of binding antigen or hapten. The present invention also includes single chain antibodies and humanized hybrid antibodies wherein amino acid sequences of a non-human donor antibody exhibiting a desired antigen-specificity are combined with sequences of a human acceptor antibody. The donor sequences will usually include at least the antigen-binding amino acid residues of the donor but may comprise other structurally and/or functionally relevant amino acid residues of the donor antibody as well. Such hybrids can be prepared by several methods well known in the art. Preferably, the binding agent or agent binds specifically to the pep-tide or polypeptide. Specific binding according to the present invention means that the ligand or agent should not bind substantially to ("cross-react" with) another peptide, polypeptide or substance present in the sample to be analyzed. Preferably, the specifically bound peptide or polypeptide should be bound with at least 3 times higher, more preferably at least 10 times higher and even more preferably at least 50 times higher affinity than any other relevant peptide or polypeptide. Non-specific binding may be tolerable, if it can still be distinguished and measured unequivocally, e.g. according to its size on a Western Blot, or by its relatively higher abundance in the sample.

Binding of the binding agent can be measured by any method known in the art. Preferably, said method is semi-quantitative or quantitative. Further suitable techniques for the determination of a polypeptide or peptide are described in the following.

Binding of a binding agent may be measured directly, e.g. by NMR or surface plasmon resonance. Measurement of the binding of a binding agent, according to preferred embodiments, is performed by an analyzer unit of a system disclosed herein. Thereafter, a level of the measured binding may be calculated by a computing device of a system disclosed herein. If the binding agent also serves as a substrate of an enzymatic activity of the pep-tide or polypeptide of interest, an enzymatic reaction product may be measured (e.g. the level of a protease can be measured by measuring the level of cleaved substrate, e.g. on a Western Blot). Alternatively, the binding agent may exhibit enzymatic properties itself and the "binding agent/peptide or polypeptide" complex or the binding agent which was bound by the peptide or polypeptide, respectively, may be contacted with a suitable substrate allowing detection by the generation of an intensity signal. For measurement of enzymatic reaction products, preferably the level of substrate is saturating. The substrate may also be labeled with a detectable label prior to the reaction. Preferably, the sample is contacted with the substrate for an adequate period of time. An adequate period of time refers to the time necessary for a detectable, preferably measurable, level of product to be produced. Instead of measuring the level of product, the time necessary for appearance of a given (e.g. detectable) level of product can be measured. Third, the binding agent may be coupled covalently or non-covalently to a label allowing detection and measurement of the binding agent. Labeling may be done by direct or indirect methods. Direct labeling involves coupling of the label directly (covalently or non-covalently) to the binding agent. Indirect labeling involves binding (covalently or non-covalently) of a secondary binding agent to the first binding agent. The secondary binding agent should specifically bind to the first binding agent. Said secondary binding agent may be coupled with a suitable label and/or be the target (receptor) of tertiary binding agent binding to the secondary binding agent. The use of secondary, tertiary or even higher order binding agents is often used to increase the signal. Suitable secondary and higher order binding agents may include antibodies, secondary antibodies, and the well-known streptavidin-biotin system (Vector La-boratories, Inc.). The binding agent or substrate may also be "tagged" with one or more tags as known in the art. Such tags may then be targets for higher order binding agents. Suitable tags include biotin, digoxygenin, His-Tag, Gluta-thion-S-Transferase, FLAG, GFP, myc-tag, influenza A virus haemagglutinin (HA), maltose binding protein, and the like. In the case of a peptide or polypeptide, the tag is preferably at the N-terminus and/or C-terminus. Suitable labels are any labels detectable by an appropriate detection method. Typical labels include gold particles, latex beads, acridan ester, luminol, ruthenium, enzymatically active labels, radioactive labels, magnetic labels ("e.g. magnetic beads", including paramagnetic and superparamagnetic labels), and fluo-rescent labels. Enzymatically active labels include e.g. horse-radish peroxidase, alkaline phosphatase, beta-Galactosidase, Luciferase, and derivatives thereof. Suitable substrates for detection include di-amino-benzidine (DAB), 3,3'-5,5'-te-tramethylbenzidine, NBT-BCIP (4-nitro blue tetrazolium chloride and 5-bromo-4-chloro-3-indolyl-phosphate, available as ready-made stock solution from Roche Diagnostics), CDP-Star™ (Amersham Bio-sciences), ECF™ (Amersham Biosciences). A suitable enzyme-substrate combination may result in a colored reaction product, fluorescence or chemoluminescence, which can be measured according to methods known in the art (e.g. using a light-sensitive film or a suit-able camera system). As for measuring the enzymatic reaction, the criteria given above apply analogously. Typical fluorescent labels include fluorescent proteins (such as GFP and its derivatives), Cy3, Cy5, Texas Red, Fluorescein, and the Alexa dyes (e.g. Alexa 568). Further fluorescent labels are available e.g. from Molecular Probes (Oregon). Also the use of quantum dots as fluorescent labels is contemplated. A radioactive label can be detected by any method known and appropriate, e.g. a light-sensitive film or a phosphor imager.

The level of a peptide or polypeptide may be, also preferably, determined as follows: (a) contacting a solid support comprising a binding agent for the peptide or polypeptide as specified above with a sample comprising the peptide or polypeptide and (b) measuring the level peptide or polypeptide which is bound to the support. The binding agent, preferably chosen from the group consisting of nucleic acids, peptides, polypeptides, antibodies and aptamers, is preferably present on a solid support in immobilized form. Materials for manufacturing solid supports are well known in the art and include, inter alia, commercially available column materials, polystyrene beads, latex beads, magnetic beads, colloid metal particles, glass and/or silicon chips and surfaces, nitrocellulose strips, membranes, sheets, duracytes, wells and walls of reaction trays, plastic tubes etc. The binding agent or agent may be bound to many different carriers. Examples of well-known carriers include glass, polystyrene, polyvinyl chloride, polypropylene, polyethylene, polycarbonate, dextran, nylon, amyloses, natural and modified celluloses, polyacrylamides, agaroses, and magnetite. The nature of the carrier can be either soluble or insoluble for the purposes of the invention. Suitable methods for fixing/immobilizing said binding agent are well known and include, but are not limited to ionic, hydrophobic, covalent interactions and the like. It is also contemplated to use "suspension arrays" as arrays according to the present invention (Nolan 2002, Trends Biotechnol. 20(1):9-12). In such suspension arrays, the carrier, e.g. a mi-crobead or microsphere, is present in suspension. The array consists of different microbeads or microspheres, possibly labeled, carrying different binding agents. Methods of producing such arrays, for example based on solid-phase chemistry and photo-labile protective groups, are generally known (U.S. Pat. No. 5,744,305).

In an embodiment of the method of the present invention, the levels of the biomarkers as referred to herein are measured by using the assays described in the Examples section.

In another embodiment of the method of the present invention, the measurement in step a) may be carried out by an analyzer unit, in particular by an analyzer unit as defined elsewhere herein.

The term "binding agent" refers to a molecule that comprises a binding moiety which specifically binds the corresponding to the respective biomarker. Examples of "binding agent" are a aptamer, antibody, antibody fragment, peptide, peptide nucleic acid (PNA) or chemical compound.

The term "specific binding" or "specifically bind" refers to a binding reaction wherein binding pair molecules exhibit a binding to each other under conditions where they do not significantly bind to other molecules. The term "specific binding" or "specifically binds", when referring to a protein or peptide as biomarker, refers to a binding reaction wherein a binding agent binds to the corresponding biomarker with an affinity of at least 10-7 M. The term "specific binding" or "specifically binds" preferably refers to an affinity of at least $10^{-8}$ M or even more preferred of at least $10^{-9}$ M for its target molecule. The term "specific" or "specifically" is used to indicate that other molecules present in the sample do not significantly bind to the binding agent specific for the target molecule. Preferably, the level of binding to a molecule other than the target molecule results in a binding affinity which is only 10% or less, more preferably only 5% or less of the affinity to the target molecule.

Examples of "binding agents" are a nucleic acid probe, nucleic acid primer, DNA molecule, RNA molecule, aptamer, antibody, antibody fragment, peptide, peptide nucleic acid (PNA) or chemical compound. A preferred binding agent is an antibody which specifically binds to the biomarker to be measured. The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity. Preferably, the antibody is a polyclonal antibody. More preferably, the antibody is a monoclonal antibody.

Another binding agent that can be applied, in an aspect, may be an aptamere which specifically binds to the at least one marker in the sample. The term "specific binding" or "specifically binds", when referring to a nucleic acid aptamer as a binding agent, refers to a binding reaction wherein a nucleic acid aptamer binds to the corresponding target molecule with an affinity in the low nM to pM range.

In yet an aspect the, sample is removed from the complex formed between the binding agent and the at least one marker prior to the measurement of the level of formed complex. Accordingly, in an aspect, the binding agent may be immobilized on a solid support. In yet an aspect, the sample can be removed from the formed complex on the solid support by applying a washing solution. The formed complex shall be proportional to the level of the at least one marker present in the sample. It will be understood that the specificity and/or sensitivity of the binding agent to be applied defines the degree of proportion of at least one marker comprised in the sample which is capable of being specifically bound. Further details on how the determination can be carried out are also found elsewhere herein. The level of formed complex shall be transformed into a level of at least one marker reflecting the level indeed present in the sample. Such a level, in an aspect, may be essentially the amount present in the sample or may be, in another aspect, an amount which is a certain proportion thereof due to the relationship between the formed complex and the amount present in the original sample.

The term "level" as used herein encompasses the absolute amount of a biomarker as referred to herein, the relative amount or concentration of the said biomarker as well as any value or parameter which correlates thereto or can be derived therefrom. Such values or parameters comprise intensity signal values from all specific physical or chemical properties obtained from the said peptides by direct measurements, e.g., intensity values in mass spectra or NMR spectra. Moreover, encompassed are all values or parameters which are obtained by indirect measurements specified elsewhere in this description, e.g., response amounts determined from biological read out systems in response to the peptides or intensity signals obtained from specifically bound ligands. It is to be understood that values correlating to the aforementioned amounts or parameters can also be obtained by all standard mathematical operations.

The term "comparing" as used herein refers to comparing the level of the biomarkers in the sample from the individual or patient with the reference level of the biomarkers specified elsewhere in this description. It is to be understood that comparing as used herein usually refers to a comparison of corresponding parameters or values, e.g., an absolute amount is compared to an absolute reference amount while a concentration is compared to a reference concentration or an intensity signal obtained from the biomarker in a sample is compared to the same type of intensity signal obtained from a reference sample. The comparison may be carried out manually or computer assisted. Thus, the comparison may be carried out by a computing device (e.g., of a system disclosed herein). The value of the measured or detected level of the biomarker in the sample from the individual or patient and the reference level can be, e.g., compared to each other and the said comparison can be automatically carried out by a computer program executing an algorithm for the comparison. The computer program carrying out the said evaluation will provide the desired assessment in a suitable output format. For a computer assisted comparison, the value of the determined amount may be compared to values corresponding to suitable references which are stored in a database by a computer program. The computer program may further evaluate the result of the comparison, i.e. automatically provide the desired assessment in a suitable output format. For a computer assisted comparison, the value of the determined amount may be compared to values corresponding to suitable references which are stored in a database by a computer program. The computer program may further evaluate the result of the comparison, i.e. automatically provides the desired assessment in a suitable output format.

In certain embodiments, the term "reference level" herein refers to a predetermined value for the respective biomarker. In this context "level" encompasses the absolute amount, the relative amount or concentration as well as any value or parameter which correlates thereto or can be derived therefrom. Preferably, the reference level is a level which allows for allocating the patient into a group of patients being eligible to intensification of heart failure therapy, or into a group of patients not being eligible to intensification of heart failure therapy. Thus, the reference level shall allow for differentiating between a patient who is eligible to intensification of heart failure therapy and a patient who is not eligible to intensification of heart failure therapy.

As the skilled artisan will appreciate the reference level is predetermined and set to meet routine requirements in terms of e.g. specificity and/or sensitivity. These requirements can vary, e.g. from regulatory body to regulatory body. It may for example be that assay sensitivity or specificity, respectively, has to be set to certain limits, e.g. 80%, 90%, 95% or 98%, respectively. These requirements may also be defined in terms of positive or negative predictive values. Nonetheless, based on the teaching given in the present invention it will always be possible for a skilled artisan to arrive at the reference level meeting those requirements. In one embodiment the reference level is determined in a reference sample or samples from a patient (or group of patients) having heart failure and being eligible to intensification of heart failure therapy or in a reference sample or samples from a patient (or group of patients) having heart failure and not being eligible to intensification of heart failure therapy. The reference level in one embodiment has been predetermined in reference samples from the disease entity to which the patient belongs. In certain embodiments the reference level can e.g. be set to any percentage between 25% and 75% of the overall distribution of the values in a disease entity investigated. In other embodiments the reference level can e.g. be set to the median, tertiles or quartiles as determined from the overall distribution of the values in reference samples from a disease entity investigated. In one embodiment the reference level is set to the median value as determined from the overall distribution of the values in a disease entity investigated. The reference level may vary depending on various physiological parameters such as age, gender or subpopulation, as well as on the means used for the determination of the biomarkers referred to herein. In one embodiment, the reference sample is from essentially the same type of cells, tissue, organ or body fluid source as the sample from the individual or patient subjected to the method of the invention, e.g. if according to the invention blood is used as a sample to determine the level of biomarkers in the individual, the reference level is also determined in blood or a part thereof.

In certain embodiments, the term "larger than the reference level" or "above the reference level" refers to a level of the biomarker in the sample from the individual or patient above the reference level or to an overall increase of 5%, 10%, 20%, 25%, 30%, 40%, 50%, 60%, 70%, 80%, 85%, 90%, 95%, 100% or greater, determined by the methods described herein, as compared to the reference level. In certain embodiments, the term increase refers to the increase in biomarker level in the sample from the individual or patient wherein, the increase is at least about 1.5-, 1.75-, 2-, 3-, 4-, 5-, 6-, 7-, 8-, 9-, 10-, 15-, 20-, 25-, 30-, 40-, 50-, 60-, 70-, 75-, 80-, 90-, or 100-fold higher as compared to the reference level, e.g. predetermined from a reference sample.

In certain embodiments, the term "lower than the reference level" or "below" herein refers to a level of the biomarker in the sample from the individual or patient below the reference level or to an overall reduction of 5%, 10%, 20%, 25%, 30%, 40%, 50%, 60%, 70%, 80%, 85%, 90%, 95%, 96%, 97%, 98%, 99% or greater, determined by the methods described herein, as compared to the reference level. In certain embodiments, the term decrease in biomarker level in the sample from the individual or patient wherein the decreased level is at most about 0.9-, 0.8-, 0.7-, 0.6-, 0.5-, 0.4-, 0.3-, 0.2-, 0.1-, 0.05-, or 0.01-fold of the reference level, e.g. predetermined from a reference sample, or lower.

The following applies as diagnostic algorithm if the at least one marker is selected from the group consisting of creatinine, urea, glucose, HbA1c (glycated hemoglobin), CRP (C-reactive protein, in particular high sensitive CRP), Cystatin C, IL-6 (Interleukin 6), Prealbumin, sFlt-1 (soluble fms-like tyrosine kinase-1), uric acid, GDF-15 (Growth Differentiation Factor 15), Galectin-3 (Gal-3), Endostatin, Mimecan, sST2 (soluble ST2), and Osteopontin: Preferably, a level (levels) of the at least one marker in the sample from the patient which is above the reference level (reference levels) for said marker (markers) indicates that the patient is eligible to intensification of heart failure therapy, and/or a level (levels) of the at least one marker in the sample from the patient which is below the reference level (reference levels) for said marker (markers) indicates that the patient is not eligible to intensification of heart failure therapy.

The following applies as diagnostic algorithm if the at least one marker is selected from the group consisting of sodium, hemoglobin, hematocrit, and IGFBP-7:

Preferably, a level (levels) of the at least one marker in the sample from the patient which is below the reference level (reference levels) for said marker (markers) indicates that the patient is eligible to intensification of heart failure therapy, and/or a level (levels) of the at least one marker in the sample from the patient which is above the reference level (reference levels) for said marker (markers) indicates that the patient is not eligible to intensification of heart failure therapy.

The following table A provides preferred ranges for reference levels (third column) for the various markers as well as preferred specific reference levels (fourth column). The person skilled in the art can determine further reference levels without further ado.

TABLE A

| Marker | Units | reference level within the range of from | reference level |
|---|---|---|---|
| Creatinine | mg/dL | about 1.2 to 1.8 | about 1.5 |
| BUN (urea) | mmol/L | about 10 to 12 | about 11.1 |
| Glucose | mmol/L | about 10 to 13 | about 11.6 |
| HbA1c | % | about 0.05 to 0.07 | about 0.06 |
| hsCRP | mg/mL | about 9 to 13 | about 10.4 |
| Cystatin C | mg/L | about 1.8 to 2.0 | about 1.9 |
| IL-6 | pg/mL | about 8 to 10 | about 9.1 |
| Prealbumin | g/L | about 0.14 to 0.18 | about 0.16 |
| sFLt-1 | pg/mL | about 85 to 100 | about 87 |
| Uric Acid | mg/dL | about 9 to 10 | about 9.1 |
| GFD-15 | pg/mL | about 2500 to 5000 | about 3210 |
| sST2 | ng/mL | about 38 to 47 | about 41.5 |
| Galectin-3 | ng/mL | about 24 to 30 | about 25 |
| Endostatin | ng/mL | about 230 to 277 | about 243 |
| Mimecan | ng/mL | about 44 to 50 | about 45.2 |
| IGFBP-7 | ng/mL | about 70 to 77 | about 71.4 |
| Osteopontin | ng/mL | about 110 to 120 | about 113.5 |
| Hemoglobin | g/dL | about 7.5 to 8.5 | about 8.04 |
| Hematocrit | % | about 0.37 to 0.43 | about 0.40 |
| QRS duration | ms | about 140 to 180 | about 160 |
| Sodium | mmol/L | about 138 to 142 | about 141 |

As regards to the QRS duration, the reference may be in the range of about 140 to about 180 ms. In an embodiment, the reference is about 160 ms.

In the context of the present invention, it is envisaged to measure the level of a single marker, or of a combination of markers. Thus, it is envisaged to measure the level of two, three, four or of even more markers. Preferred combinations are as follows:

For example, the following marker combinations are envisaged:
creatinine and sodium
hemoglobin and QRS duration
urea and HbA1c
hematocrit and creatinine In accordance with the present invention, the level of a certain marker may be measured in order to identify a patient who is eligible to intensification of a certain heart failure therapy, in particular the intensified treatment with a certain medicament. For example, a marker may be used in order to assess whether the treatment with the medicament shall be intensified or not (e.g. whether the dosage of the administered medicament shall be increased or not). For example, if the marker to be measured is creatinine, the heart failure therapy to be intensified, preferably is treatment with a beta blocker.

The definitions given herein above apply mutatis mutandis to the following. Also, the steps carried out in connection with the method described herein above, may be carried out in accordance with the following method.

The present invention also relates to a method, in particular an in vitro method, for identifying a patient who is eligible to an intensification of heart failure therapy, said method comprising the step of
  (a) measuring the level of a BNP-type peptide in a in a sample from a patient who has heart failure and who receives BNP-type peptide guided heart failure therapy;
  (b) measuring the level of at least one marker selected from the group consisting of creatinine, urea, sodium, glucose, HbA1c (glycated hemoglobin), hemoglobin, hematocrit, CRP (C-reactive protein, in particular high sensitive CRP), Cystatin C, IL-6 (Interleukin 6), Pre-albumin, sFlt-1 (soluble fms-like tyrosine kinase-1), uric acid, GDF-15 (Growth Differentiation Factor 15), Galectin-3 (Gal-3), Endostatin, Mimecan, IGFBP7 (Insulin Growth Factor Binding Protein 7), sST2 (soluble ST2), and Osteopontin in a sample from the patient,
  (c) comparing the level of the BNP-type peptide measured in (a) to a reference level (or reference levels), and
  (d) comparing the level (or levels) of the at least one marker measured in (b) to a reference level (or reference levels).

By carrying out steps (c) or (d), a patient who is eligible to intensification of heart failure therapy is identified. In an embodiment, the method further comprises step (e) of identifying or selecting a patient who is eligible to an intensification of heart failure therapy. In addition, the method may comprise step (f) of intensifying heart failure therapy or recommending intensification of heart failure therapy (if the patient is identified as to be eligible to intensification of heart failure therapy). Accordingly, the present invention also envisages also a method of intensifying heart failure therapy, said method comprising steps (a) to (f) as set forth above.

In addition the a marker as referred to step a), or alternatively, the QRS duration may be measured or provided and compared to the a reference (as outlined elsewhere herein)

In addition to the method describe above, the method further comprises the step of measuring the level of a BNP-type peptide.

As used herein, the term "BNP-type peptides" comprise pre-proBNP, proBNP, NT-proBNP, and BNP. The pre-pro peptide (134 amino acids in the case of pre-proBNP) comprises a short signal peptide, which is enzymatically cleaved off to release the pro peptide (108 amino acids in the case of proBNP). The pro peptide is further cleaved into an N-terminal pro peptide (NT-pro peptide, 76 amino acids in case of NT-proBNP) and the active hormone (32 amino acids in the case of BNP). Preferably, BNP-type peptides according to the present invention are NT-proBNP, BNP (brain natriuretic peptide), and variants thereof. BNP is the active hormone and has a shorter half-life than the respective inactive counterpart NT-proBNP. BNP is metabolized in the blood, whereas NT-proBNP circulates in the blood as an intact molecule and as such is eliminated renally. The in-vivo half-life of NT-proBNP is 120 min longer than that of BNP, which is 20 min (Smith 2000, J Endocrinol. 167: 239-46.). Preanalytics are more robust with NT-proBNP allowing easy transportation of the sample to a central laboratory (Mueller 2004, Clin Chem Lab Med 42: 942-4.). Blood samples can be stored at room temperature for several days or may be mailed or shipped without recovery loss. In contrast, storage of BNP for 48 hours at room temperature or at 4° Celsius leads to a concentration loss of at least 20% (Mueller loc.cit.; Wu 2004, Clin Chem 50: 867-73.). Therefore, depending on the time-course or properties of interest, either measurement of the active or the inactive forms of the natriuretic peptide can be advantageous. The most preferred BNP-type peptides according to the present invention are NT-proBNP or variants thereof. As briefly discussed above, the human NT-proBNP, as referred to in accordance with the present invention, is a polypeptide comprising, preferably, 76 amino acids in length corresponding to the N-terminal portion of the human NT-proBNP molecule. The structure of the human BNP and NT-proBNP has been described already in detail in the prior art, e.g., WO 02/089657, WO 02/083913 or Bonow loc. cit. Preferably, human NT-proBNP as used herein is human NT-proBNP as disclosed in EP 0 648 228 B1. These prior art documents are herewith incorporated by reference with respect to the specific sequences of NT-proBNP and variants thereof disclosed therein. The NT-proBNP referred to in accordance with the present invention further encompasses allelic and other variants of said specific sequence for human NT-proBNP discussed above. Specifically, envisaged are variant polypeptides which are on the amino acid level preferably, at least 50%, 60%, 70%, 80%, 85%, 90%, 92%, 95%, 97%, 98%, or 99% identical to human NT-proBNP, preferably over the entire length of human NT-proBNP. The degree of identity between two amino acid sequences can be determined by algorithms well known in the art. Preferably, the degree of identity is to be determined by comparing two optimally aligned sequences over a comparison window, where the fragment of amino acid sequence in the comparison window may comprise additions or deletions (e.g., gaps or overhangs) as compared to the reference sequence (which does not comprise additions or deletions) for optimal alignment. The percentage is calculated by determining the number of positions at which the identical amino acid residue occurs in both sequences to yield the number of matched positions, dividing the number of matched positions by the total number of positions in the window of comparison and multiplying the result by 100 to yield the percentage of sequence identity. Optimal alignment of sequences for comparison may be conducted by the local homology algorithm of Smith and Waterman Add. APL. Math. 2:482 (1981), by the homology alignment algorithm of Needleman and Wunsch J. Mol. Biol. 48:443 (1970), by the search for similarity method of Pearson and Lipman Proc. Natl. Acad. Sci. (USA) 85: 2444 (1988), by computerized implementations of these algorithms (GAP, BESTFIT, BLAST, PASTA, and TFASTA in the Wisconsin Genetics Software Package, Genetics Computer Group (GCG), 575 Science Dr., Madison, Wis.), or by visual inspection. Given that two sequences have been identified for comparison, GAP and BESTFIT are preferably employed to determine their optimal alignment and, thus, the degree of identity. Preferably, the default values of 5.00 for gap weight and 0.30 for gap weight length are used. Variants referred to above may be allelic variants or any other species specific homologs, paralogs, or orthologs. Substantially similar and also envisaged are proteolytic degradation products which are still recognized by the diagnostic means or by ligands directed against the respective full-length peptide. Also encompassed are variant polypeptides having amino acid deletions, substitutions, and/or additions compared to the amino acid sequence of human NT-proBNP as long as the said polypeptides have NT-proBNP properties. NT-proBNP properties as referred to herein are immunological and/or biological properties. Preferably, the NT-proBNP variants have immunological properties (i.e. epitope composition) comparable to those of human NT-proBNP. Thus, the variants shall be recognizable by the aforementioned means or ligands used for determination of the amount of the natriuretic peptides. Biological and/or immunological NT-proBNP properties can be detected by the assay described in Karl et al. (Karl 1999, Scand J Clin Lab Invest 230:177-181), Yeo et al. (Yeo 2003, Clinica Chimica Acta 338:107-115). Also, an assay for the determination of NT-proBNP is described by Mueller T. et al., Clinica Chimica Acta 341 (2004) 41-48. In an embodiment, the NT-proBNP is carried out as described any one of the aforementioned references. Variants also include posttranslationally modified peptides such as glycosylated peptides. Further, a variant in accordance with the present invention is also a peptide or polypeptide which has been modified after collection of the sample, for example by covalent or non-covalent attachment of a label, particularly a radioactive or fluorescent label, to the peptide.

The term "reference level" has been defined above. The reference level for the BNP-type peptide, preferably, shall be a level which when taken alone (i.e. not in combination with the further markers as referred in the context of the present invention) which is indicative for a patient who is not eligible to an intensification of heart failure therapy. Preferred reference levels for said BNP-type peptide being indicative of intensification of heart failure therapy to be applied in the context of the present invention are those described in the Examples. Preferred reference levels are within a range from about 80 to 400 pg/ml, or, in particular, from about 80 to 200 pg/ml for BNP, and within a range from about 450 to 2200 pg/ml, or in particular from about 800 pg/ml to 1200 pg/ml for NT-proBNP. Further preferred reference levels are about 100 pg/ml or 400 pg/ml for BNP, and about 1000 or 1200 pg/ml for NT-proBNP.

Preferred reference levels or ranges for references levels for the markers creatinine, urea, sodium, glucose, HbA1c (glycated hemoglobin), hemoglobin, hematocrit, CRP (C-reactive protein, in particular high sensitive CRP), Cystatin C, IL-6 (Interleukin 6), Prealbumin, sFlt-1 (soluble fms-like tyrosine kinase-1), uric acid, GDF-15 (Growth Differentiation Factor 15), Galectin-3 (Gal-3), Endostatin, Mimecan, IGFBP7 (Insulin Growth Factor Binding Protein 7), sST2 (soluble ST2), and Osteopontin (OPN) are shown in Table A above.

The following applies as diagnostic algorithm if the at least one marker as measured in step (b) is selected from the group consisting of creatinine, urea, glucose, HbA1c (glycated hemoglobin), CRP (C-reactive protein, in particular high sensitive CRP), Cystatin C, IL-6 (Interleukin 6), Prealbumin, sFlt-1 (soluble fms-like tyrosine kinase-1), uric acid, GDF-15 (Growth Differentiation Factor 15), Galectin-3 (Gal-3), Endostatin, Mimecan, sST2 (soluble ST2), and Osteopontin:

(a) a level of the at least one marker in the sample from the patient which is above the reference level for said marker, and a level of BNP-type peptide which is above the reference level for said BNP-type peptide is indicative for a patient who is eligible to intensification of heart failure therapy, (b) a level of the at least one marker in the sample from the patient which is above the reference level for said marker, and a level of said BNP-type peptide which is below the reference level for said BNP-type peptide is indicative for a patient who is eligible to intensification of heart failure therapy, (c) a level of the at least one marker in the sample from the patient which is below the reference level for said marker, and a level of said BNP-type peptide which is above the reference level for said BNP-type peptide is indicative for a patient who is eligible to intensification of heart failure therapy, and/or (d) a level of the at least one marker in the sample from the patient which is below the reference level for said marker, and a level of said BNP-type peptide which is below the reference level for said BNP-type peptide is indicative for a patient who is not eligible to intensification of heart failure therapy.

Alternatively or additionally, the following applies as diagnostic algorithm if the at least one marker as measured in step (b) is selected from the group consisting of sodium, hemoglobin, hematocrit, and IGFBP-7:

(a) a level of the at least one marker in the sample from the patient which is below the reference level for said marker, and a level of said BNP-type peptide which is above the reference level for said BNP-type peptide is indicative for a patient who is eligible to intensification of heart failure therapy, (b) a level of the at least one marker in the sample from the patient which is below the reference level for said marker, and a level of said BNP-type peptide which is below the reference level for said BNP-type peptide is indicative for a patient who is eligible to intensification of heart failure therapy, (c) a level of the at least one marker in the sample from the patient which is above the reference level for said marker, and a level of said BNP-type peptide which is above the reference level for said BNP-type peptide is indicative for a patient who is eligible to intensification of heart failure therapy, and/or (d) a level of the at least one marker in the sample from the patient which is above the reference level for said marker, and a level of said BNP-type peptide which is below the reference level for said BNP-type peptide is indicative for a patient who is not eligible to intensification of heart failure therapy.

The patient to be tested in accordance with the aforementioned method may display any level (in particular any blood, serum or plasma level) of a BNP-type peptide.

Moreover, the present invention relates to a method for optimizing BNP-type peptide guided heart failure therapy, said method comprising the steps of (a) measuring the level of at least one marker selected from the group consisting of creatinine, urea, sodium, glucose, HbA1c (glycated hemoglobin), hemoglobin, hematocrit, CRP (C-reactive protein, in particular high sensitive CRP), Cystatin C, IL-6 (Interleukin 6), Prealbumin, sFlt-1 (soluble fms-like tyrosine kinase-1), uric acid, GDF-15 (Growth Differentiation Factor 15), Galectin-3 (Gal-3), Endostatin, Mimecan, IGFBP7 (Insulin Growth Factor Binding Protein 7), sST2 (soluble ST2), and Osteopontin in a sample from a patient who has heart failure and who receives BNP-type peptide guided therapy, and (b) comparing the level (or levels) of the marker (or markers) measured in (a) to a reference level (or reference levels), thereby optimizing BNP-type peptide guided therapy.

The patient in accordance with the aforementioned method preferably displays a level (in particular a blood, serum or plasma level) of a BNP-type peptide which is below the reference level for said BNP-type peptide being indicative of intensification of heart failure therapy.

The definitions given herein above apply mutatis mutandis to the following embodiments of the present invention.

Methods for Predicting the Risk of Cardiac Decompensation, Hospitalization and/or Mortality Further, the present invention is directed to a method, in particular an in vitro method, for predicting the risk of a patient who has heart failure and who receives BNP-type peptide guided heart failure therapy to suffer from cardiac decompensation, hospitalization, and/or mortality (death) said method comprising the steps of (a) measuring the level of at least one marker selected from the group consisting of creatinine, urea, sodium, glucose, HbA1c (glycated hemoglobin), hemoglobin, hematocrit, CRP (C-reactive protein, in particular high sensitive CRP), Cystatin C, IL-6 (Interleukin 6), Prealbumin, sFlt-1 (soluble fms-like tyrosine kinase-1), uric acid, GDF-15 (Growth Differentiation Factor 15), Galectin-3 (Gal-3), Endostatin, Mimecan, IGFBP7 (Insulin Growth Factor Binding Protein 7), sST2 (soluble ST2), and Osteopontin in a sample from a patient who has heart failure and who receives BNP-type peptide guided heart failure therapy, and (b) comparing the level (or levels) of the marker (or markers) measured in (a) to a reference level (or reference levels).

The method may further comprise the step of (c) predicting (or providing a prediction of) the risk of the patient to suffer from cardiac decompensation, hospitalization, and/or mortality, in particular wherein a level (levels) of the at least one marker above or below the reference level (levels) indicates that the patient has an increased risk to suffer from cardiac decompensation, hospitalization, and/or mortality, and wherein a level (levels) of the at least one marker above or below the reference level (levels) indicates that the patient has a decreased risk to suffer from cardiac decompensation, hospitalization, and/or mortality.

In a preferred embodiment, the patient displays a level (in particular a blood, serum or plasma level) of a BNP-type peptide which is below the reference level for said BNP-type peptide being indicative of intensification of heart failure therapy.

The following applies as diagnostic algorithm:

The following applies as diagnostic algorithm if the at least one marker is selected from the group consisting of creatinine, urea, glucose, HbA1c (glycated hemoglobin), CRP (C-reactive protein, in particular high sensitive CRP), Cystatin C, IL-6 (Interleukin 6), Prealbumin, sFlt-1 (soluble fms-like tyrosine kinase-1), uric acid, GDF-15 (Growth Differentiation Factor 15), Galectin-3 (Gal-3), Endostatin, Mimecan, sST2 (soluble ST2), and Osteopontin:

Preferably, a level (levels) of the at least one marker in the sample from the patient which is above the reference level (reference levels) for said marker (markers) indicates that the patient has an increased risk to suffer from cardiac decompensation, hospitalization, and/or mortality, and/or wherein a level (levels) of the at least one marker in the sample from the patient which is below the reference level (reference levels) for said marker (markers) indicates that the patient has a decreased risk to suffer from cardiac decompensation, hospitalization, and/or mortality.

The following applies as diagnostic algorithm if the at least one marker is selected from the group consisting of sodium, hemoglobin, hematocrit, and IGFBP-7:

Preferably, a level (levels) of the at least one marker in the sample from the patient which is below the reference level (reference levels) for said marker (markers) indicates that the patient has an increased risk to suffer from cardiac decompensation, hospitalization, and/or mortality, and/or wherein a level (levels) of the at least one marker in the sample from the patient which is above the reference level (reference levels) for said marker (markers) indicates that the patient has a decreased risk to suffer from cardiac decompensation, hospitalization, and/or mortality.

Preferred reference levels or ranges of reference levels are disclosed elsewhere herein (see Table A).

The phrase "providing a predication" as used herein refers to using the information or data generated relating to the level of the at least one biomarker in a sample of the patient as referred to herein to predict the risk of the patient to suffer from cardiac decompensation, hospitalization, and/or mortality. The information or data may be in any form, written, oral or electronic. In some embodiments, using the information or data generated includes communicating, presenting, reporting, storing, sending, transferring, supplying, transmitting, dispensing, or combinations thereof. In some embodiments, communicating, presenting, reporting, storing, sending, transferring, supplying, transmitting, dispensing, or combinations thereof are performed by a computing device, analyzer unit or combination thereof. In some further embodiments, communicating, presenting, reporting, storing, sending, transferring, supplying, transmitting, dispensing, or combinations thereof are performed by a laboratory or medical professional. In some embodiments, the information or data includes a comparison of the level of the at least one marker to a reference level. In some embodiments, the information or data includes an indication that the patient at risk or not at risk to suffer from cardiac decompensation, hospitalization, and/or mortality.

The present invention also relates to a method, in particular an in vitro method for predicting the risk of a patient who has heart failure and who receives BNP-type peptide guided heart failure therapy to suffer from cardiac decompensation, hospitalization, and/or mortality (death), said method comprising the step of (a) measuring the level of a BNP-type peptide in a in a sample from a patient who has heart failure and who receives BNP-type peptide guided heart failure therapy;

(b) measuring the level of at least one marker selected from the group consisting of creatinine, urea, sodium, glucose, HbA1c (glycated hemoglobin), hemoglobin, hematocrit, CRP (C-reactive protein, in particular high sensitive CRP), Cystatin C, IL-6 (Interleukin 6), Prealbumin, sFlt-1 (soluble fms-like tyrosine kinase-1), uric acid, GDF-15 (Growth Differentiation Factor 15), Galectin-3 (Gal-3), Endostatin, Mimecan, IGFBP7 (Insulin Growth Factor Binding Protein 7), sST2 (soluble ST2), and Osteopontin in a sample from the patient, (c) comparing the level of the BNP-type peptide measured in (a) to a reference level (or reference levels), and (d) comparing the level (or levels) of the at least one marker measured in (b) to a reference level (or reference levels).

The method may further comprise the step of (f) predicting (or providing a prediction of) the risk of the patient to suffer from cardiac decompensation, hospitalization, and/or mortality. The prediction is preferably based on the results of the comparison steps.

The patient to be tested in accordance with the aforementioned method may display any level (in particular any blood, serum or plasma level) of a BNP-type peptide.

The following applies as diagnostic algorithm if the at least one marker as measured in step (b) is selected from the group consisting of creatinine, urea, glucose, HbA1c (glycated hemoglobin), CRP (C-reactive protein, in particular high sensitive CRP), Cystatin C, IL-6 (Interleukin 6), Prealbumin, sFlt-1 (soluble fms-like tyrosine kinase-1), uric acid, GDF-15 (Growth Differentiation Factor 15), Galectin-3 (Gal-3), Endostatin, Mimecan, sST2 (soluble ST2), and Osteopontin:

(a) a level of the at least one marker in the sample from the patient which is above the reference level for said marker, and a level of BNP-type peptide which is above the reference level for said BNP-type peptide is indicative for a patient who has an increased risk to suffer from cardiac decompensation, hospitalization, and/or mortality, (b) a level of the at least one marker in the sample from the patient which is above the reference level for said marker, and a level of said BNP-type peptide which is below the reference level for said BNP-type peptide is indicative for a patient who has an increased risk to suffer from cardiac decompensation, hospitalization, and/or mortality, (c) a level of the at least one marker in the sample from the patient which is below the reference level for said marker, and a level of said BNP-type peptide which is above the reference level for said BNP-type peptide is indicative for a patient who has an increased risk to suffer from cardiac decompensation, hospitalization, and/or mortality, and/or (d) a level of the at least one marker in the sample from the patient which is below the reference level for said marker, and a level of said BNP-type peptide which is below the reference level for said BNP-type peptide is indicative for a patient who has a decreased risk to suffer from cardiac decompensation, hospitalization, and/or mortality.

Alternatively or additionally, the following applies as diagnostic algorithm if the at least one marker as measured in step (b) is selected from the group consisting of sodium, hemoglobin, hematocrit, and IGFBP-7:

(a) a level of the at least one marker in the sample from the patient which is below the reference level for said marker, and a level of said BNP-type peptide which is above the reference level for said BNP-type peptide is indicative for a patient who has an increased risk to suffer from cardiac decompensation, hospitalization, and/or mortality, (b) a level of the at least one marker in the sample from the patient which is below the reference level for said marker, and a level of said BNP-type peptide which is below the reference level for said BNP-type peptide is indicative for a patient who has an increased risk to suffer from cardiac decompensation, hospitalization, and/or mortality, (c) a level of the at least one marker in the sample from the patient which is above the reference level for said marker, and a level of said BNP-type peptide which is above the reference level for said BNP-type peptide is indicative for a patient who has an increased risk to suffer from cardiac decompensation, hospitalization, and/or mortality and/or (d) a level of the at least one marker in the sample from the patient which is above the reference level for said marker, and a level of said BNP-type peptide which is below the reference level for said BNP-type peptide is indicative for a patient who has a decreased risk to suffer from cardiac decompensation, hospitalization, and/or mortality.

Preferred reference levels or ranges of reference levels are disclosed elsewhere herein (see e.g. table A).

The term "cardiac decompensation" is well known in the art. Preferably, the term refers to a condition of chronic heart failure in which the heart is unable to ensure adequate cellular perfusion in all parts of the body without assistance. Accordingly, the compensatory mechanisms of the body are no longer sufficient to maintain pump function.

The term "mortality" as used herein relates to any kind of mortality, in particular mortality which is caused by a cardiovascular complication. Preferably, said mortality is caused by heart failure.

The term "hospitalization" is well known in the art. As used herein, term relates to hospitalization which is caused by a cardiovascular complication. Preferably, said hospitalization is caused by heart failure.

The term "predicting" used herein refers to assessing the probability according to which a patient as referred to herein will suffer from cardiac decompensation, hospitalization, and/or mortality within a defined time window (predictive window) in the future. The predictive window is an interval in which the patient will develop cardiac decompensation, will be hospitalized and/or will die according to the predicted probability. The predictive window may be the entire remaining lifespan of the patient upon analysis by the method of the present invention. Preferably, however, the predictive window is an interval of one, two, three, four, five, ten, fifteen or 20 years after the method of the present invention has been carried out (more preferably and precisely, after the sample to be analyzed by the method of the present invention has been obtained). Most preferably, said predictive window is an interval of four or five years. As will be understood by those skilled in the art, such an assessment is usually not intended to be correct for 100% of the patients to be analyzed. The term, however, requires that the assessment will be valid for a statistically significant portion of the patients to be analyzed. Whether a portion is statistically significant can be determined without further ado by the person skilled in the art using various well known statistic evaluation tools, e.g., determination of confidence intervals, p-value determination, Student's t-test, Mann-Whitney test, etc. Details are found in Dowdy and Wearden, Statistics for Research, John Wiley & Sons, New York 1983. Preferred confidence intervals are at least 90%, at least 95%, at least 97%, at least 98% or at least 99%. The p-values are, preferably, 0.1, 0.05, 0.01, 0.005, or 0.0001. Preferably, the probability envisaged by the present invention allows that the prediction will be correct for at least 60%, at least 70%, at least 80%, or at least 90% of the patients of a given cohort.

The expression "predicting the risk of cardiac decompensation, hospitalization, or death" as used herein means that it the patient to be analyzed by the method of the present invention is allocated either into the group of patients of a population having an increased risk, or into a group having a reduced risk. An increased risk as referred to in accordance with the present invention, preferably, means that the risk of developing cardiac decompensation, of hospitalization, or of mortality within a predetermined predictive window is increased significantly (i.e. increased significantly) for a patient with respect to the average risk for a such an event in a population of patients having heart failure and receiving BNP-type peptide guided therapy. A reduced risk as referred to in accordance with the present invention, preferably, means that the risk of developing cardiac decompensation, of hospitalization, or of mortality within a predetermined predictive window is reduced significantly for a patient with respect to the average risk for such an event in a population of said patients. Particularly, a significant increase or reduction of a risk is an increase or reduction or a risk of a size which is considered to be significant for prognosis, particularly said increase or reduction is considered statistically significant. The terms "significant" and "statistically significant" are known by the person skilled in the art. Thus, whether an increase or reduction of a risk is significant or statistically significant can be determined without further ado by the person skilled in the art using various well known statistic evaluation tools.

Preferably, for a predictive window of tree years, an increased risk is within the range of 3.0% and 19.0%, more preferably within the range of 12.0% to 17.0%, most preferably, within the range of 8.0% to 16.0%. An increased, and, thus increased risk as used herein, preferably, relates to a risk of more than 3.0%, preferably, more than 12.0%, more preferably, more than 17%, even more preferably, more than 20%, preferably, with respect to a predictive window of three years. A reduced risk as used herein, preferably, relates to a risk of less than 8.0%, preferably, less than 6%, even more preferably, less than 4%, and is, most preferably within the range of 3.0% and 8.0%, preferably with respect to a predictive window of three years.

The present invention also relates to the use of at least one marker selected from the group consisting of creatinine, urea, sodium, glucose, HbA1c (glycated hemoglobin), CRP (C-reactive protein, in particular high sensitive CRP), Cystatin C, IL-6 (Interleukin 6), Prealbumin, sFlt-1 (soluble fms-like tyrosine kinase-1), uric acid, GDF-15 (Growth Differentiation Factor 15), Galectin-3 (Gal-3), Endostatin, Mimecan, sST2 (soluble ST2), and Osteopontin, and/or the use of at least one detection agent for said at least one marker (i.e. for creatinine, urea, sodium, glucose, HbA1c (glycated hemoglobin), CRP (C-reactive protein, in particular high sensitive CRP), Cystatin C, IL-6 (Interleukin 6), Prealbumin, sFlt-1 (soluble fms-like tyrosine kinase-1), uric acid, GDF-15 (Growth Differentiation Factor 15), Galectin-3 (Gal-3), Endostatin, Mimecan, sST2 (soluble ST2), or Osteopontin) in a sample of a patient having heart failure and receiving BNP-type peptide guided heart failure therapy for identifying a patient being eligible to intensification of heart failure therapy, for predicting the risk of the patient of suffering from cardiac decompensation, of hospitalization, and or of mortality, or for optimizing BNP-type peptide guided heart failure therapy.

The present invention also relates to the i) use of the QRS duration, optionally in combination with a BNP-type peptide, and/or the use of a device for determining the QRS duration such as an ECG device (i.e. a device which can generate an electrocardiogram), optionally in combination with at least one detection agent for a BNP-type peptide, for identifying a patient being eligible to intensification of heart failure therapy, for predicting the risk of the patient of suffering from cardiac decompensation, of hospitalization, and or of mortality, or for optimizing BNP-type peptide guided heart failure therapy. As outlined elsewhere herein, the patient shall receive BNP-type peptide guided heart failure therapy.

The present invention also relates to the use of a BNP-type peptide in combination with at least one marker selected from the group consisting of creatinine, urea, sodium, glucose, HbA1c (glycated hemoglobin), CRP (C-reactive protein, in particular high sensitive CRP), Cystatin C, IL-6 (Interleukin 6), Prealbumin, sFlt-1 (soluble fms-like tyrosine kinase-1), uric acid, GDF-15 (Growth Differentiation Factor 15), Galectin-3 (Gal-3), Endostatin, Mimecan, sST2 (soluble ST2), and Osteopontin, and/or the use of an detection agent which specifically binds to a BNP-type peptide in combination of at least one detection agent for a marker selected from the group of marker selected from the group consisting of creatinine, urea, sodium, glucose, HbA1c (glycated hemoglobin), CRP (C-reactive protein, in particular high sensitive CRP), Cystatin C, IL-6 (Interleukin 6), Prealbumin, sFlt-1 (soluble fms-like tyrosine kinase-1), uric acid, GDF-15 (Growth Differentiation Factor 15), Galectin-3 (Gal-3), Endostatin, Mimecan, sST2 (soluble ST2), and Osteopontin, in a sample of a patient having heart failure and receiving BNP-type peptide guided heart failure therapy for identifying a patient being eligible to intensification of heart failure therapy, or for predicting the risk of the patient of suffering from cardiac decompensation, of hospitalization, or of mortality.

The present invention further relates to the use of at least one marker selected from the group consisting of creatinine, urea, sodium, glucose, HbA1c (glycated hemoglobin), hemoglobin, hematocrit, IGFBP7, CRP (C-reactive protein, in particular high sensitive CRP), Cystatin C, IL-6 (Interleukin 6), Prealbumin, sFlt-1 (soluble fms-like tyrosine kinase-1), uric acid, GDF-15 (Growth Differentiation Factor 15), Galectin-3 (Gal-3), Endostatin, Mimecan, sST2 (soluble ST2), and Osteopontin, and/or the use of at least one detection agent for said at least one marker (i.e. for creatinine, urea, sodium, glucose, HbA1c (glycated hemoglobin), hemoglobin, hematocrit, IGFBP7, CRP (C-reactive protein, in particular high sensitive CRP), Cystatin C, IL-6 (Interleukin 6), Prealbumin, sFlt-1 (soluble fms-like tyrosine kinase-1), uric acid, GDF-15 (Growth Differentiation Factor 15), Galectin-3 (Gal-3), Endostatin, Mimecan, sST2 (soluble ST2), or Osteopontin) for the manufacture of a diagnostic composition for identifying a patient being eligible to intensification of heart failure therapy, or for predicting the risk of the patient of suffering from cardiac decompensation, of hospitalization, or of mortality (in particular, in a sample of a patient having heart failure and receiving BNP-type peptide guided heart failure therapy).

The present invention also relates to the use of a BNP-type peptide in combination with at least one marker selected from the group consisting of creatinine, urea, sodium, glucose, HbA1c (glycated hemoglobin), hemoglobin, hematocrit, IGFBP7, CRP (C-reactive protein, in particular high sensitive CRP), Cystatin C, IL-6 (Interleukin 6), Prealbumin, sFlt-1 (soluble fms-like tyrosine kinase-1), uric acid, GDF-15 (Growth Differentiation Factor 15), Galectin-3 (Gal-3), Endostatin, Mimecan, sST2 (soluble ST2), and Osteopontin, and/or the use of an detection agent which specifically binds to a BNP-type peptide in combination with at least one detection agent for a marker selected from the group of marker selected from the group consisting of creatinine, urea, sodium, glucose, HbA1c (glycated hemoglobin), hemoglobin, hematocrit, IGFBP7, CRP (C-reactive protein, in particular high sensitive CRP), Cystatin C, IL-6 (Interleukin 6), Prealbumin, sFlt-1 (soluble fms-like tyrosine kinase-1), uric acid, GDF-15 (Growth Differentiation Factor 15), Galectin-3 (Gal-3), Endostatin, Mimecan, sST2 (soluble ST2), and Osteopontin, for the manufacture of a diagnostic composition for identifying a patient being eligible to intensification of heart failure therapy, or for predicting the risk of the patient of suffering from cardiac decompensation, of hospitalization, or of mortality (in particular, in a sample of a patient having heart failure and receiving BNP-type peptide guided heart failure therapy).

If the marker is a polypeptide or peptide, in particular if the marker is HbA1c (glycated hemoglobin), CRP (C-reactive protein, in particular high sensitive CRP), Cystatin C, IL-6 (Interleukin 6), Prealbumin, sFlt-1 (soluble fms-like tyrosine kinase-1), uric acid, GDF-15 (Growth Differentiation Factor 15), Galectin-3 (Gal-3), Endostatin, Mimecan, sST2 (soluble ST2), and Osteopontin, the detection agent preferably specifically binds to said marker. In this case, the detection agent is preferably a monoclonal or polyclonal antibody (for a definition of the term "antibody" see elsewhere herein). For the remaining markers, the detection agent may be an agent that forms an complex with the marker thereby allowing the measurement of the level of the marker, or enzyme that allows for the conversion of the marker as described elsewhere herein.

If the marker is creatinine, the detection agent may be picric acid which forms a complex with creatinine.

If the marker is uric acid, the detection agent may be uricase or peroxidase.

If the marker is urea, the detection agent may be urease.

If the marker is glucose, the detection agent may be a hexokinase.

According, the present invention also preferably relates to a system for identifying a patient who is eligible to an intensification of heart failure therapy, comprising
  a) an analyzer unit configured to contact, in vitro, a portion of a sample from the patient with a detection agent (or agents if the level of at least one marker is measured) for measuring the level of at least one marker selected from the group consisting of creatinine, urea, sodium, glucose, HbA1c (glycated hemoglobin), hemoglobin, hematocrit, CRP (C-reactive protein, in particular high sensitive CRP), Cystatin C, IL-6 (Interleukin 6), Prealbumin, sFlt-1 (soluble fms-like tyrosine kinase-1), uric acid, GDF-15 (Growth Differentiation Factor 15), Galectin-3 (Gal-3), Endostatin, Mimecan, IGFBP7 (Insulin Growth Factor Binding Protein 7), sST2 (soluble ST2), and Osteopontin,
  b) an analyzer unit configured to detect a signal from the portion of the sample from the patient contacted with the agent (or agents),
  c) a computing device having a processor and in operable communication with said analysis units, and
  d) a non-transient machine readable media including a plurality of instruction executable by a the processor, the instructions, when executed calculate a level of the at least one marker, and compare the level of the at least one marker with a reference level (or reference levels if the level of more than one marker is measured), thereby identifying a patient who is eligible to an intensification of heart failure therapy.

As set forth above, the patient shall have heart failure and shall receive BNP-type peptide guided heart failure therapy.

Furthermore, a device adapted for carrying out the method of the present invention is provided, said device comprising
  a) an analyzer unit comprising a detection agent (or agents) for measuring the level of at least one marker selected from the group consisting of creatinine, urea, sodium, glucose, HbA1c (glycated hemoglobin), hemoglobin, hematocrit, CRP (C-reactive protein, in particular high sensitive CRP), Cystatin C, IL-6 (Interleukin 6), Prealbumin, sFlt-1 (soluble fms-like tyrosine kinase-1), uric acid, GDF-15 (Growth Differentiation Factor 15), Galectin-3 (Gal-3), Endostatin, Mimecan, IGFBP7 (Insulin Growth Factor Binding Protein 7), sST2 (soluble ST2), and Osteopontin in a sample of a patient who has heart failure and who receives BNP-type peptide guided heart failure therapy, and
  b) an analyzer unit for comparing the measured level(s) with reference level(s), whereby a patient is identified who is eligible to an intensification of heart failure therapy antagonist, a diuretic, and an inhibitor of the renin-angiotensin system, said unit comprising a database with a reference level (or levels) and a computer-implemented algorithm carrying out the comparison.

Preferred reference levels and diagnostic algorithms are disclosed elsewhere herein.

A preferred embodiment of the instant disclosure includes a system for identifying a subject being eligible to the administration of at least one medicament selected from the group consisting of a beta blocker, an aldosterone antagonist, a diuretic, and an inhibitor of the renin-angiotensin system. Examples of systems include clinical chemistry analyzers, coagulation chemistry analyzers, immunochemistry analyzers, urine analyzers, nucleic acid analyzers, used to detect the result of chemical or biological reactions or to monitor the progress of chemical or biological reactions. More specifically, exemplary systems of the instant disclosure may include Roche Elecsys™ Systems and Cobas® e Immunoassay Analyzers, Abbott Architect™ and Axsym™ Analyzers, Siemens Centaur™ and Immulite™ Analyzers, and Beckman Coulter UniCel™ and Acess™ Analyzers, or the like.

Embodiments of the system may include one or more analyzer units utilized for practicing the subject disclosure. The analyzer units of the system disclosed herein are in operable communication with the computing device disclosed herein through any of a wired connection, Bluetooth, LANS, or wireless signal, as are known. Additionally, according to the instant disclosure, an analyzer unit may comprise a stand-alone apparatus, or module within a larger instrument, which performs one or both of the detection, e.g. qualitative and/or quantitative evaluation of samples for diagnostic purpose. For example, an analyzer unit may perform or assist with the pipetting, dosing, mixing of samples and/or reagents. An analyzer unit may comprise a reagent holding unit for holding reagents to perform the assays. Reagents may be arranged for example in the form of containers or cassettes containing individual reagents or group of reagents, placed in appropriate receptacles or positions within a storage compartment or conveyor. Detection reagents may also be in immobilized form on a solid support which are contacted with the sample. Further, an analyzer unit may include a process and/or detection component which is optimizable for specific analysis.

According to some embodiments, an analyzer unit may be configured for optical detection of an analyte, for example a marker, with a sample. An exemplary analyzer unit configured for optical detection comprises a device configured for converting electro-magnetic energy into an electrical signal, which includes both single and multi-element or array optical detectors. According to the present disclosure, an optical detector is capable of monitoring an optical electromagnetic signal and providing an electrical outlet signal or response signal relative to a baseline signal indicative of the presence and/or concentration of an analyte in a sample being located in an optical path. Such devices may also include, for example, photodiodes, including avalanche photodiodes, phototransistors, photoconductive detectors, linear sensor arrays, CCD detectors, CMOS detectors, including CMOS array detectors, photomultipliers, and photomultiplier arrays. According to certain embodiments, an optical detector, such as a photodiode or photomultiplier, may contain additional signal conditioning or processing electronics. For example, an optical detector may include at least one pre-amplifier, electronic filter, or integrated circuit. Suitable pre-preamplifiers include, for example, integrating, transimpedance, and current gain (current mirror) pre-amplifiers.

Additionally, one or more analyzer unit according to the instant disclosure may comprise a light source for emitting light. For example, a light source of an analyzer unit may consist of at least one light emitting element (such as a light emitting diode, an electric powered radiation source such as an incandescent lamp, an electroluminescent lamp, a gas discharge lamp, a high-intensity discharge lamp, a laser) for measuring analyte concentrations with a sample being tested or for enabling an energy transfer (for example, through florescent resonance energy transfer or catalyzing an enzyme).

Further, an analyzer unit of the system may include one or more incubation units (for example, for maintaining a sample or a reagent at a specified temperature or temperature range). In some embodiments, an analyzer unit may include a thermocycler, include a real-time thermocycler, for subjecting a sample to repeated temperature cycles and monitoring a change in the level of an amplification product with the sample.

Additionally, an analyzer unit of the system disclosed herein may comprise, or be operationally connected to, a reaction vessel or cuvette feeding unit. Exemplary feeding units include liquid processing units, such as a pipetting unit, to deliver samples and/or reagents to the reaction vessels. The pipetting unit may comprise a reusable washable needle, e.g. a steel needle, or disposable pipette tips. The analyzer unit may further comprise one or more mixing units, for example a shaker to shake a cuvette comprising a liquid, or a mixing paddle to mix liquids in a cuvette, or reagent container.

It follows from the above that according to some embodiments of the instant disclosure, portions of some steps of methods disclosed and described herein may be performed by a computing device. A computing device may be a general purpose computer or a portable computing device, for example. It should also be understood that multiple computing devices may be used together, such as over a network or other methods of transferring data, for performing one or more steps of the methods disclosed herein. Exemplary computing devices include desktop computers, laptop computers, personal data assistants ("PDA"), such as BLACKBERRY brand devices, cellular devices, tablet computers, servers, and the like. In general, a computing device comprises a processor capable of executing a plurality of instructions (such as a program of software).

A computing device has access to a memory. A memory is a computer readable medium and may comprise a single storage device or multiple storage devices, located either locally with the computing device or accessible to the computing device across a network, for example. Computer-readable media may be any available media that can be accessed by the computing device and includes both volatile and non-volatile media. Further, computer readable-media may be one or both of removable and non-removable media. By way of example, and not limitation, computer-readable media may comprise computer storage media. Exemplary computer storage media includes, but is not limited to, RAM, ROM, EEPROM, flash memory or any other memory technology, CD-ROM, Digital Versatile Disk (DVD) or other optical disk storage, magnetic cassettes, magnetic tape, magnetic disk storage or other magnetic storage devices, or any other medium which can be used for storing a plurality of instructions capable of being accessed by the computing device and executed by the processor of the computing device.

According to embodiments of the instant disclosure, software may include instructions which, when executed by a processor of the computing device, may perform one or more steps of the methods disclosed herein. Some of the instructions may be adapted to produce signals that control operation of other machines and thus may operate through those control signals to transform materials far removed from the computer itself. These descriptions and representations are the means used by those skilled in the art of data processing, for example, to most effectively convey the substance of their work to others skilled in the art.

The plurality of instructions may also comprise an algorithm which is generally conceived to be a self-consistent sequence of steps leading to a desired result. These steps are those requiring physical manipulations of physical quantities. Usually, though not necessarily, these quantities take the form of electrical or magnetic pulses or signals capable of being stored, transferred, transformed, combined, compared, and otherwise manipulated. It proves convenient at times, principally for reasons of common usage, to refer to these signals as values, characters, display data, numbers, or the like as a reference to the physical items or manifestations in which such signals are embodied or expressed. It should be borne in mind, however, that all of these and similar terms are to be associated with the appropriate physical quantities and are merely used here as convenient labels applied to these quantities. According to some embodiments of the instant disclosure, an algorithm for carrying out a comparison between a determined level of one or more markers disclosed herein, and a suitable reference, is embodied and performed by executing the instructions. The results may be given as output of parametric diagnostic raw data or as absolute or relative levels. According to various embodiments of the system disclosed herein, a "diagnosis" may be provided by the computing device of a system disclosed herein based on said comparison of the calculated "level" to a reference or a threshold. For example, a computing device of a system may provide an indicator, in the form of a word, symbol, or numerical value which is indicative of a particular diagnosis.

The computing device may also have access to an output device. Exemplary output devices include fax machines, displays, printers, and files, for example. According to some embodiments of the present disclosure, a computing device may perform one or more steps of a method disclosed herein, and thereafter provide an output, via an output device, relating to a result, indication, ratio or other factor of the method.

Finally, the invention pertains to a kit adapted for carrying out a method of the present invention comprising at least a detection agent (or agents if the level of at least one marker is measured) for measuring the level of at least one marker selected from the group consisting of creatinine, urea, sodium, glucose, HbA1c (glycated hemoglobin), hemoglobin, hematocrit, CRP (C-reactive protein, in particular high sensitive CRP), Cystatin C, IL-6 (Interleukin 6), Prealbumin, sFlt-1 (soluble fms-like tyrosine kinase-1), uric acid, GDF-15 (Growth Differentiation Factor 15), Galectin-3 (Gal-3), Endostatin, Mimecan, IGFBP7 (Insulin Growth Factor Binding Protein 7), sST2 (soluble ST2), and Osteopontin, reference standards as well as instructions for carrying out the said method.

The term "kit" as used herein refers to a collection of the aforementioned components, preferably, provided in separately or within a single container. The container also comprises instructions for carrying out the method of the present invention. These instructions may be in the form of a manual or may be provided by a computer program code which is capable of carrying out the comparisons referred to in the methods of the present invention and to establish a diagnosis accordingly when implemented on a computer or a data processing device. The computer program code may be provided on a data storage medium or device such as a optical storage medium (e.g., a Compact Disc) or directly on a computer or data processing device. Further, the kit shall comprise at least one standard for a reference as defined herein above, i.e. a solution with a pre-defined level for the biomarker as referred to herein representing a reference level.

In some embodiments, a kit disclosed herein includes at least one component or a packaged combination of components for practicing a disclosed method. By "packaged combination" it is meant that the kits provide a single package that contains a combination of one or more components, such as probes (for example, an antibody), controls, buffers, reagents (for example, conjugate and/or substrate) instructions, and the like, as disclosed herein. A kit containing a single container is also included within the definition of "packaged combination." In some embodiments, the kits include at least one probe, for example an antibody (having specific affinity for an epitope of a biomarker as disclosed herein. For example, the kits may include an antibody that is labelled with a fluorophore or an antibody that is a member of a fusion protein. In the kit, the probe may be immobilized, and may be immobilized in a specific conformation. For example, an immobilized probe may be provided in a kit to specifically bind target protein, to detect target protein in a sample, and/or to remove target protein from a sample.

According to some embodiments, kits include at least one probe, which may be immobilized, in at least one container. Kits may also include multiple probes, optionally immobilized, in one or more containers. For example, the multiple probes may be present in a single container or in separate containers, for example, wherein each container contains a single probe.

In some embodiments, a kit may include one or more non-immobilized probe and one or more solid support that does or does not include an immobilized probe. Some such embodiments may comprise some or all of the reagents and supplies needed for immobilizing one or more probes to the solid support, or some or all of the reagents and supplies needed for binding of immobilized probes to specific proteins within a sample.

In certain embodiments, a single probe (including multiple copies of the same probe) may be immobilized on a single solid support and provided in a single container. In other embodiments, two or more probes, each specific for a different target protein or a different form of a single target protein (such as a specific epitope), a provided in a single container. In some such embodiments, an immobilized probe may be provided in multiple different containers (e.g., in single-use form), or multiple immobilized probes may be provided in multiple different containers. In further embodiments, the probes may be immobilized on multiple different type of solid supports. Any combination of immobilized probe(s) and container(s) is contemplated for the kits disclosed herein, and any combination thereof may be selected to achieve a suitable kit for a desired use.

A container of the kits may be any container that is suitable for packaging and/or containing one or more components disclosed herein, including for example probes (for example, an antibody), controls, buffers, and reagents (for example, conjugate and/or substrate). Suitable materials include, but are not limited to, glass, plastic, cardboard or other paper product, wood, metal, and any alloy thereof. In some embodiments, the container may completely encase an immobilized probe(s) or may simply cover the probe to minimize contamination by dust, oils, etc., and expose to light. In some further embodiments, he kits may comprise a single container or multiple containers, and where multiple containers are present, each container may be the same as all other containers, different than others, or different than some but not all other containers.

PREFERRED EMBODIMENTS OF THE PRESENT INVENTION

In the following, preferred embodiments of the present invention are disclosed. The definitions and explanations given herein above and in the claims apply mutatis mutandis.

1. A method for identifying a patient who is eligible to an intensification of heart failure therapy, said method comprising the steps of
    (a) measuring the level of at least one marker selected from the group consisting of creatinine, urea, sodium, glucose, HbA1c (glycated hemoglobin), hemoglobin, hematocrit, CRP (C-reactive protein, in particular high sensitive CRP), Cystatin C, IL-6 (Interleukin 6), Prealbumin, sFlt-1 (soluble fms-like tyrosine kinase-1), uric acid, GDF-15 (Growth Differentiation Factor 15), Galectin-3 (Gal-3), Endostatin, Mimecan, IGFBP7 (Insulin Growth Factor Binding Protein 7), sST2 (soluble ST2), and Osteopontin in a sample from a patient who has heart failure and who receives BNP-type peptide guided heart failure therapy, and
    (b) comparing the level (or levels) of the marker (or markers) measured in (a) to a reference level (or reference levels).
2. The method according to embodiment 1, further comprising step (c) of identifying a patient who is eligible to an intensification of heart failure therapy, or not.
3. The method of embodiment 1 or 2, wherein the patient displays a level of a BNP-type peptide which is below the reference level for said BNP-type peptide being indicative of intensification of heart failure therapy.
4. The method according to any one of embodiments 1 to 4, wherein
    i) the at least one marker is selected from the group consisting of creatinine, urea, glucose, HbA1c (glycated hemoglobin), CRP (C-reactive protein, in particular high sensitive CRP), Cystatin C, IL-6 (Interleukin 6), Prealbumin, sFlt-1 (soluble fms-like tyrosine kinase-1), uric acid, GDF-15 (Growth Differentiation Factor 15), Galectin-3 (Gal-3), Endostatin, Mimecan, sST2 (soluble ST2), and Osteopontin, and wherein a level (levels) of the at least one marker in the sample from the patient which is above the reference level (reference levels) for said marker (markers) indicates that the patient is eligible to intensification of heart failure therapy, and/or wherein a level (levels) of the at least one marker in the sample from the patient which is below the reference level (reference levels) for said marker (markers) indicates that the patient is not eligible to intensification of heart failure therapy, and/or
    ii) the at least one marker is selected from the group consisting of sodium, hemoglobin, hematocrit, and IGFBP-7, and wherein a level (levels) of the at least one marker in the sample from the patient which is below the reference level (reference levels) for said marker (markers) indicates that the patient is eligible to intensification of heart failure therapy, and/or wherein a level (levels) of the at least one marker in the sample from the patient which is above the reference level (reference levels) for said marker (markers) indicates that the patient is not eligible to intensification of heart failure therapy.

5. A method for identifying a patient who is eligible to an intensification of heart failure therapy, said method comprising the step of
   (a) measuring the level of a BNP-type peptide in a sample from a patient who has heart failure and who receives BNP-type peptide guided heart failure therapy;
   (b) measuring the level of at least one marker selected from the group consisting of creatinine, urea, sodium, glucose, HbA1c (glycated hemoglobin), hemoglobin, hematocrit, CRP (C-reactive protein, in particular high sensitive CRP), Cystatin C, IL-6 (Interleukin 6), Prealbumin, sFlt-1 (soluble fms-like tyrosine kinase-1), uric acid, GDF-15 (Growth Differentiation Factor 15), Galectin-3 (Gal-3), Endostatin, Mimecan, IGFBP7 (Insulin Growth Factor Binding Protein 7), sST2 (soluble ST2), and Osteopontin in a sample from the patient,
   (c) comparing the level of the BNP-type peptide measured in (a) to a reference level (or reference levels), and
   (d) comparing the level (or levels) of the at least one marker measured in (b) to a reference level (or reference levels).

6. The method according to embodiment 5, wherein
   i) the at least one marker is selected from the group consisting of creatinine, urea, glucose, HbA1c (glycated hemoglobin), CRP (C-reactive protein, in particular high sensitive CRP), Cystatin C, IL-6 (Interleukin 6), Prealbumin, sFlt-1 (soluble fms-like tyrosine kinase-1), uric acid, GDF-15 (Growth Differentiation Factor 15), Galectin-3 (Gal-3), Endostatin, Mimecan, sST2 (soluble ST2), and Osteopontin, and wherein
      (a) a level of the at least one marker in the sample from the patient which is above the reference level for said marker, and a level of BNP-type peptide which is above the reference level for said BNP-type peptide is indicative for a patient who is eligible to intensification of heart failure therapy,
      (b) a level of the at least one marker in the sample from the patient which is above the reference level for said marker, and a level of said BNP-type peptide which is below the reference level for said BNP-type peptide is indicative for a patient who is eligible to intensification of heart failure therapy,
      (c) a level of the at least one marker in the sample from the patient which is below the reference level for said marker, and a level of said BNP-type peptide which is above the reference level for said BNP-type peptide is indicative for a patient who is eligible to intensification of heart failure therapy, and/or
      (d) a level of the at least one marker in the sample from the patient which is below the reference level for said marker, and a level of said BNP-type peptide which is below the reference level for said BNP-type peptide is indicative for a patient who is not eligible to intensification of heart failure therapy, and/or
   ii) the at least one marker is selected from the group consisting of sodium, hemoglobin, hematocrit, and IGFBP-7,
      (a) a level of the at least one marker in the sample from the patient which is below the reference level for said marker, and a level of said BNP-type peptide which is above the reference level for said BNP-type peptide is indicative for a patient who is eligible to intensification of heart failure therapy,
      (b) a level of the at least one marker in the sample from the patient which is below the reference level for said marker, and a level of said BNP-type peptide which is below the reference level for said BNP-type peptide is indicative for a patient who is eligible to intensification of heart failure therapy,
      (c) a level of the at least one marker in the sample from the patient which is above the reference level for said marker, and a level of said BNP-type peptide which is above the reference level for said BNP-type peptide is indicative for a patient who is eligible to intensification of heart failure therapy, and/or
      (d) a level of the at least one marker in the sample from the patient which is above the reference level for said marker, and a level of said BNP-type peptide which is below the reference level for said BNP-type peptide is indicative for a patient who is not eligible to intensification of heart failure therapy.

7. A method for optimizing BNP-type peptide guided heart failure therapy, said method comprising the steps of
   (a) measuring the level of at least one marker selected from the group consisting of creatinine, urea, sodium, glucose, HbA1c (glycated hemoglobin), hemoglobin, hematocrit, CRP (C-reactive protein, in particular high sensitive CRP), Cystatin C, IL-6 (Interleukin 6), Prealbumin, sFlt-1 (soluble fms-like tyrosine kinase-1), uric acid, GDF-15 (Growth Differentiation Factor 15), Galectin-3 (Gal-3), Endostatin, Mimecan, IGFBP7 (Insulin Growth Factor Binding Protein 7), sST2 (soluble ST2), and Osteopontin in a sample from a patient who has heart failure and who receives BNP-type peptide guided therapy, and
   (b) comparing the level (or levels) of the marker (or markers) measured in (a) to a reference level (or reference levels), thereby optimizing BNP-type peptide guided therapy.

8. The method according to any one of embodiments 1 to 7, wherein the patient is human.

9. The method according to any one of embodiments to 1 to 8, wherein the patient has heart failure classified as stage B or C according to the ACC/AHA classification, and/or wherein the patient has heart failure according to class II or III of the NYHA classification.

10. The method according to any one of embodiments 1 to 9, wherein the sample is a blood, serum or plasma sample.

11. The method according to any one of embodiments 1 to 10, wherein the heart failure therapy is medicinal heart failure therapy, in particular wherein the heart failure therapy comprises administration of at least one medicament selected from the group consisting of diuretics, angiotensin converting enzyme inhibitors, angiotensin II receptor blockers, beta blockers and aldosterone antagonists.

12. The method of embodiment 11, wherein the heart failure therapy comprises combined administration of a beta blocker and an ACE inhibitor.

13. The method according to any one of embodiments 1 to 12, wherein the intensification of heart failure therapy comprises increasing the dosage of previously administered medicaments, the administration of a further medicament (or medicaments), in particular the administration of a further medicament (or medicaments) having a different mode of action that the previously administered medicaments, device therapy, life style changes, and combinations thereof.

14. Use of i) at least one marker selected from the group consisting of creatinine, urea, sodium, glucose, HbA1c (glycated hemoglobin), hemoglobin, hematocrit, IGFBP7, CRP (C-reactive protein, in particular high sensitive CRP), Cystatin C, IL-6 (Interleukin 6), Prealbumin, sFlt-1 (soluble fms-like tyrosine kinase-1), uric acid, GDF-15 (Growth Differentiation Factor 15), Galectin-3 (Gal-3), Endostatin, Mimecan, sST2 (soluble ST2), and Osteopontin, and/or use of ii) at least one detection agent for said at least one marker in a sample of a patient having heart failure and receiving BNP-type peptide guided heart failure therapy for identifying a patient being eligible to intensification of heart failure therapy, for predicting the risk of the patient of suffering from cardiac decompensation, of hospitalization, and/or of mortality, or for optimizing BNP-type peptide guided heart failure therapy.

15. Use of a BNP-type peptide in combination with at least one marker selected from the group consisting of creatinine, urea, sodium, glucose, HbA1c (glycated hemoglobin), hemoglobin, hematocrit, IGFBP7, CRP (C-reactive protein, in particular high sensitive CRP), Cystatin C, IL-6 (Interleukin 6), Prealbumin, sFlt-1 (soluble fms-like tyrosine kinase-1), uric acid, GDF-15 (Growth Differentiation Factor 15), Galectin-3 (Gal-3), Endostatin, Mimecan, sST2 (soluble ST2), and Osteopontin, and/or the use of an detection agent which specifically binds to a BNP-type peptide in combination with at least one detection agent for a marker selected from the group of marker selected from the group consisting of creatinine, urea, sodium, glucose, HbA1c (glycated hemoglobin), hemoglobin, hematocrit, IGFBP7, CRP (C-reactive protein, in particular high sensitive CRP), Cystatin C, IL-6 (Interleukin 6), Prealbumin, sFlt-1 (soluble fms-like tyrosine kinase-1), uric acid, GDF-15 (Growth Differentiation Factor 15), Galectin-3 (Gal-3), Endostatin, Mimecan, sST2 (soluble ST2), and Osteopontin, in a sample of a patient having heart failure and receiving BNP-type peptide guided heart failure therapy for identifying a patient being eligible to intensification of heart failure therapy, or for predicting the risk of the patient of suffering from cardiac decompensation, of hospitalization, or of death.

All references referred to above are herewith incorporated by reference with respect to their entire disclosure content as well as their specific disclosure content explicitly referred to in the above description.

EXAMPLES

The invention will now be illustrated by the following Examples which are not intended to restrict or limit the scope of this invention.

Example 1

Patients 499 patients suffering from HF (NYHA class II-IV systolic HF (LVEF ≤45%) were guided according to NT-proBNP target or usual care (Pfisterer M. et al. JAMA. 2009; 301:383-92). Overall, patients with NT-proBNP levels <1000 pg/ml, a previously identified cut-off value for good outcome, had significantly better outcome than those with NT-proBNP levels that could not be reduced to these levels. However, some of the patients with low NT-proBNP levels <1000 pg/mL remained at risk. Additionally, some patients with NT-proBNP levels slightly above 1000 pg/mL were at unexpectedly high risk. This risk could be identified with good accuracy by additional measurement of marker and clinical parameter levels, for example after 6 months of therapy. Moreover, these additional markers and parameters also provided additional important information for potential therapy guidance in the group with higher risk (i.e. NT-proBNP levels after 6 months >1000 pg/ml).

BNP and/or NT-proBNP levels together with one or several markers and/or clinical parameters are measured at regular intervals every few weeks up to every six months. If intensification of medical therapy is either clinically necessary and/or indicated by the BNP/NT-proBNP and/or one of these additional markers and/or parameters, these subjects make follow-up visits in the clinic every few weeks until either an optimal/maximal medical therapy is achieved, the BNP/NT-proBNP target goal of ≤100-200 pg/mL and ≤1,000 pg/mL, respectively, is reached, and the following target goals or the subject requires hospitalization.

Table 1 shows cutoffs for additional markers and clinical parameters (based on ROC-optimized cutoffs and inflection points of risk deciles; both methods render similar cutoffs for identification of residual risk; when both are available the lower cutoff should be applied):

TABLE 1

| Marker | Units | Parameter | |
|---|---|---|---|
| | | ROC optimized cutoff | Risk decile cutoff |
| Creatinine | mg/dL | 1.5 | Not applicable (n.a) |
| BUN (urea) | mmol/L | 12.1 | 11.1 |
| Glucose | mmol/L | n.a. | 11.6 |
| HbA1c | % | 0.06 | n.a. |
| hsCRP | mg/mL | 10.4 | 12.7 |
| Cystatin C | mg/L | 1.9 | n.a. |
| IL-6 | pg/mL | 9.3 | 9.9 |
| Prealbumin | g/L | 0.16 | n.a. |
| sFLt-1 | pg/mL | 87.3 | 94.3 |
| Uric Acid | mg/dL | 9.1 | 9.4 |
| GFD-15 | pg/mL | 4270 | 3210 |
| sST2 | ng/mL | 41.5 | 45.0 |
| Galectin-3 | ng/mL | 29.0 | 25.1 |
| Endostatin | ng/mL | 243 | 257 |
| Mimecan | ng/mL | 45.3 | 46.7 |
| IGFBP-7 | ng/mL | 75.3 | 71.4 |
| Osteopontin | ng/mL | 113.5 | 114.5 |
| Hemoglobin | g/dL | 8.04 | n.a. |
| Hematocrit | % | 0.40 | n.a. |
| QRS duration | ms | 159 | 160 |
| Sodium | mmol/L | 140.5 | 141 |

Table 2 showing Wald scores, p-values and Hazard Ratios (HR, with 95% confidence intervals) of biomarkers and clinical parameters in patients guided according to NT-proBNP. Wald scores and Hazard Ratio indicate remaining risk of decompensation, hospitalization, or death in patients guided with BNP-type peptides.

| variable | Wald | P-value | HR | 95% CI |
|---|---|---|---|---|
| Hb | 2.0 | .16 | .82 | .62-1.08 |
| creatinine | 19.9 | <.001 | 3.76 | 2.10-6.73 |
| BUN | 24.1 | <.001 | 1.10 | 1.06-1.14 |
| Hct | 2.0 | .16 | .01 | .00-5.80 |
| Glucose | 3.5 | .06 | 1.11 | 1.00-1.23 |
| HbA1c | 3.3 | .07 | n/a | n/a |
| hsCRP log | 4.3 | .04 | 1.68 | 1.03-2.75 |
| CysC | 17.8 | <.001 | 2.71 | 1.71-4.31 |
| IL6 log | 7.7 | .006 | 2.64 | 1.33-5.24 |
| PREA BL | 5.5 | .02 | .001 | .00-.32 |
| sFIT log | 3.0 | .08 | 3.20 | .86-11.84 |
| hsTnT log | 15.0 | <.001 | 3.81 | 1.94-7.48 |
| uric acid | 5.0 | .03 | 1.19 | 1.02-1.39 |
| GDF15 log | 17.9 | <.001 | 26.10 | 5.77-118.07 |
| ST2 log | 8.7 | .003 | 4.24 | 1.62-11.09 |

-continued

| variable | Wald | P-value | HR | 95% CI |
|---|---|---|---|---|
| Gal3 log | 6.8 | .009 | 6.53 | 1.59-26.83 |
| Endostatin | 8.2 | .004 | 88.43 | 4.11-1901.95 |
| Mimecan | 7.0 | <.001 | 1.03 | 1.02-1.05 |
| IGFBP7 | 6.4 | .01 | .98 | .97-1.00 |
| OPN (Osteopontin) | 2.2 | .14 | 1'005 | 1.00-1.01 |
| Sodium | 5.8 | .02 | .93 | .87-.99 |

All subjects with a BNP/NT-proBNP concentration >100-200 pg/mL and >1,000 pg/mL and marker/parameter levels above the cutoffs in the table above (or below for Hemoglobin, Hematocrit, IGFBP-7, and sodium), respectively, are considered for drug therapy and/or device therapy intensification, irrespective of symptom status, perceived stability, and with careful reassessment about the presence of an "optimal" medical program. Additionally, subjects with BNP/NT-proBNP concentration <100-200 pg/mL and <1,000 pg/mL, respectively and marker/parameter levels above the cutoffs as shown above are considered for drug therapy and/or device therapy intensification. Management of HF patients according to such guided combined marker guided HF therapy is the same as with standard-of-care and encompasses all drugs, devices, and treatment options as recommended by practice guidelines. Therapy intensification consists of increasing the dose of previously prescribed drugs or adding drugs of a different mode of action or device therapy, exercise, diet, or a combination thereof in compliance with practice guidelines and consistent with best clinical practices. No particular algorithm for drug titration or drug selection is used. Although loop diuretics may lower NT-proBNP concentrations, they are not typically be considered "first-line" therapy for a non-congested patient with an elevated NT-proBNP, given the lack of a mortality benefit of such agents in the context of chronic HF.

Once medication adjustments result in the achievement of target value or the subject is symptomatically stable, the subject is considered as being on a "combined marker-targeted optimal medical regimen" and is therefore removed from the few-week follow-up loop and is seen at the next scheduled clinic visit (regular monitoring intervals). Combined marker levels during further visits or during near patient combined marker measurements (using point of care assays) may be used to further guide HF therapy, i.e. to further increase or reduce therapy intensity in similar visit and BNP/NT-proBNP measurements loops as described above.

If a subject does not meet the combined marker/parameter target goals but does reach a clear therapeutic limit, the subject will be removed from the few-week follow-up loop and will be seen at the next scheduled clinic visit. This subject is reevaluated at that scheduled clinic visit with respect to combined marker levels and opportunities for further titration of medication and adjustment of treatment options. The invention of additional stratification according to further markers and parameters also provides benefit to patients with higher NT-proBNP targets, e.g. 3000 pg/mL. Specifically, since not all patients can reach NT-proBNP targets ≤1,000 pg/mL, higher target cutoffs may be used and at these levels, further markers and clinical parameters can still provide additional risk stratification, monitoring and therapy guidance benefits.

Compared to prior art and previous biomarker guided HF approaches, the invention provides additional marker and parameter target levels beyond BNP/NT-proBNP target ranges. The invention also improves the identification of patients that do not optimally benefit from BNP/NT-proBNP-guided HF therapy.

Furthermore, associations of marker levels, therapy modifications, and outcomes indicate that the residual risk reflected by the different parameter above can be modified using available therapies. This association indicates that the various marker combinations can be applied to guide heart failure therapy beyond NT-proBNP. One example of these therapy associations are shown below:

Combination of NT-proBNP and creatinine to guide beta blockers: Patients guided with NT-proBNP and high creatinine concentrations at 6 months experienced a good outcome with high beta blocker dose or increasing doses of beta blockers.

Example 2

Assays

NT-proBNP was determined using Roche's electrochemiluminescence ELISA sandwich test Elecsys proBNP II STAT (Short Turn Around Time) assay. The test employs two monoclonal antibodies which recognize epitopes located in the N-terminal part (1-76) of proBNP (1-108).

IL-6 (Interleukin 6) was measured by an electrochemiluminescent immunoassay (ECLIA, Roche Diagnostics). The test was performed using a Cobas E601 analyzer from Roche Diagnostics. The test is based on a first incubation with a biotinylated monoclonal IL-6-specific antibody and a second incubation with a monoclonal IL-6-specific antibody labeled with a ruthenium complex and streptavidin-coated microparticles.

High-sensitive (hs) CRP was determined using a particle enhance immunoturbidimetric assay from Roche Diagnostics (Tina-quant Cardiac C-reactive Protein (Latex) High Sensitive). In this test, Anti-CRP antibodies coupled to latex microparticles react with antigen in the sample to form an antigen/antibody complex. Following agglutination, the complex is measured turbidimetrically.

To determine the concentration of GDF-15 in serum and plasma samples, an Elecsys prototype test was employed, using a polyclonal, GDF-15 affinity chromatography-purified, goat anti-human GDF-15 IgG antibody from R&D Systems (AF957). In each experiment, a standard curve was generated with recombinant human GDF-15 from R&D Systems (957-GD/CF). The results with new batches or recombinant GDF-15 protein were tested in standard plasma samples and any deviation above 10% was corrected by introducing an adjustment factor for this assay. GDF-15 measurements in serum and plasma samples from the same patient yielded virtually identical results after correction for eventual dilution factors. The detection limit of the assay was 200 pg/ml.

For detection of IGFBP7 in human serum or plasma, a sandwich ELISA was used. For capture and detection of the antigen, aliquots of an anti-IGFBP7 polyclonal antibody from R&D Systems (Catalogue number: AF 1334) was conjugated with biotin and digoxigenin, respectively.

Streptavidin-coated 96-well microtiter plates were incubated with 100 pi biotinylated anti-IGFBP7 polyclonal antibody for 60 min at 1 pg/ml in 1×PBS solution. After incubation, plates were washed three times with 1×PBS+ 0.02% Tween 20 (Polyoxyethylene (20) sorbitan monolaurate), blocked with PBS+1% BSA (bovine serum albumen) and then washed again three times with 1×PBS+0.02% TWEEN-20 (Polyoxyethylene (20) sorbitan monolaurate).

Wells were then incubated for 1.5 h with either a serial dilution of the recombinant IGFBP7 as standard antigen or with diluted serum or plasma samples (1:50) from patients or control individuals, respectively. After binding of IGFBP7, plates were washed three times with 1×PBS+ 0.02% TWEEN-20 (Polyoxyethylene (20) sorbitan monolaurate). For specific detection of bound IGFBP7, wells were incubated with 100 µl of digoxigenylated anti-IGFBP7 polyclonal antibody for 60 min at 1 µg/ml in 1×PBS+1% BSA. Thereafter, plates were washed three times to remove unbound antibody. In a next step, wells were incubated with 75 mU/ml anti-digoxigenin-POD conjugates (Roche Diagnostics GmbH, Mannheim, Germany, Catalog No. 1633716) for 60 min in 1×PBS+1% BSA. Plates were subsequently washed six times with the same buffer. For detection of antigen-antibody complexes, wells were incubated with 100 µl ABTS solution (Roche Diagnostics GmbH, Mannheim, Germany, Catalog No. 11685767) and the optical density (OD) was measured after 15 min at 405 and 492 nm with an ELISA reader.

Gal-3 was determined by using the BGM Galectin-3 assay (BG medicine, Waltham, Mass., USA). It quantitatively measures galectin-3 in serum or EDTA-plasma by enzyme linked immunosorbent assay (ELISA) on a microtiter plate platform. The assay utilizes two monoclonal antibodies against galectin-3. One rat monoclonal anti-mouse galectin-3 antibody is coated onto the surface of the wells in a microtiter plate and serves as the capture antibody to bind galectin-3 molecules in samples, while the other mouse monoclonal anti-human galectin-3 antibody is provided in solution and functions as the tracer antibody for detecting galectin-3 molecules bound to the capture antibody.

For detection of mimecan in human serum or plasma, a sandwich ELISA was used. For capture and detection of the antigen, aliquots of an anti-mimecan polyclonal antibody from R&D Systems (Catalogue number: AF 2660) are conjugated with biotin and digoxygenin, respectively. Streptavidin-coated 96-well microtiter plates are incubated with 100 µl biotinylated anti-mimecan polyclonal antibody for 60 min at 0.2 [mu]g/ml in I×PBS solution. After incubation, plates are washed three times with 1×PBS+0.02% TWEEN-20 (Polyoxyethylene (20) sorbitan monolaurate), blocked with PBS+2% BSA (bovine serum albumen) for 45 min and then washed again three times with I×PBS+0.02% TWEEN-20 (Polyoxyethylene (20) sorbitan monolaurate). Wells are then incubated for 1 h with 100 µl of either a serial dilution of the recombinant mimecan as standard antigen or with diluted serum or plasma samples (1:5 in 1×PBS+1% BSA) from patients or control individuals, respectively. After binding of mimecan, plates are washed three times with I×PBS+0.02% TWEEN-20 (Polyoxyethylene (20) sorbitan monolaurate). For specific detection of bound mimecan, wells are incubated with 100 µl of digoxigenylated anti-mimecan polyclonal antibody for 45 min at 0.2 µg/ml in 1×PBS+1% BSA. Thereafter, plates are washed three times to remove unbound antibody. In a next step, wells are incubated with 100 µl of 75 mU/ml anti-digoxigenin-POD conjugates (Roche Diagnostics GmbH, Mannheim, Germany, Catalog No. 1633716) for 30 min in 1×PBS+1% BSA. Plates are subsequently washed six times with the same washing buffer as above. For detection of antigen-antibody complexes, wells are incubated with 100 µl ABTS solution (Roche Diagnostics GmbH, Mannheim, Germany, Catalog No. 11685767) and the optical density (OD) is measured after 15 min at 405 and 492 nm with an ELISA reader.

For measurement of endostatin in human serum or plasma, a commercially available sandwich ELISA (Quantikine Human Endostatin Immunoassay, Catalog Number DNSTO, R&D Systems) was used. Measurements are performed according to the instructions given by the manufacturer.

sST2 was determined by using the Presage™ ST2 Assay from Critical Diagnostics (San Diego, Calif., USA). The assay is a quantitative sandwich monoclonal ELISA in a 96 well plate format for measurement of ST2 in serum or plasma. Diluted plasma was loaded into appropriate wells in the anti-ST2 antibody coated plate and incubated for the prescribed time. Following a series of steps where reagents are washed from the plate, and additional reagents were added and subsequently washed out, the analyte was finally detected by addition of a colorimetric reagent and the resulting signal was measured spectroscopically at 450 nm.

The biomarker mimecan was determined as described in WO2011/012268.

sFlt1 was tested using an ELECSYS immunoassay which employs two antibodies that are specific for sFlt1. The test can be carried out automatically using different Roche analysers including ELECSYS 2010 and cobra e411 and cobra e601.

Uric acid was determined by applying an enzymatic colorimetric method. In this enzymatic reaction, the peroxide reacts in the presence of peroxidase (POD), N-ethyl-N-(2-hydroxy-3-sulfopropyl)-3-methylaniline (TOOS), and 4-aminophenazone to form a quinone-diimine dye. The intensity of the red color formed is proportional to the uric acid concentration and is determined photometrically.

Urea was measured by an in vitro test for the quantitative determination of urea/urea nitrogen in human serum, plasma and urine on Roche/Hitachi cobas c systems. The test can be carried out automatically using different analysers including cobas c 311 and cobas c 501/502. The assay is a kinetic assay with urease and glutamate dehydrogenase. Urea is hydrolyzed by urease to form ammonium and carbonate. In the second reaction 2-oxoglutarate reacts with ammonium in the presence of glutamate dehydrogenase (GLDH) and the coenzyme NADH to produce L-glutamate. In this reaction 2 moles of NADH are oxidized to $NAD^+$ for each mole of urea hydrolyzed. The rate of decrease in the NADH concentration is directly proportional to the urea concentration in the specimen and is measured photometrically.

Creatinine was measured creatinine was measured in plasma samples by a rateblanked and compensated Jaffe method adapted for Roche/Hitachi auto-analysers (see also Foster-Swanson et al., Reference Interval Studies of the Rate-Blanked Creatinine/Jaffe Method on BM/Hitachi Systems in Six U. S. Laboratories. Clin Chem 1994; Abstract No. 361). The assay is based on a kinetic in vitro test using rate-blanking and compensation for the quantitative determination of creatinine in human serum, plasma and urine. Sodium hydroxide and picric acid was added to the sample to start the formation of creatinine-picric acid complex. In alkaline solution, creatinine forms a yellow-orange complex with picrate. The color intensity which is directly proportional to the creatinine concentration was measured photometrically.

D-Glucose was measured in plasma samples using an enzymatic assay from Roche/R-Biopharm (see also Schmidt, Die enzymatische Bestimmung von Glucose and Fructose nebeneinander, Klinische Wochenzeitschrift, 1961, 39, 1244-1247). The marker was phosphorylated to D-glucose-6-phosphate in the presence of the enzyme hexokinase (HK) and adenosine-5'-triphosphate (ATP) with the simultaneous formation of adenosine-5'-diphosphate (ATP). In the presence of the enzyme glucose-6-phosphate dehydrogenase, D-glucose-6-phosphate was oxidized to by NADP to D-gluconate phosphate with the formation of reduced nicotinamide-adenine dinucleotide phosphate (NADPH). The amount of NADPH formed in this reaction is stoichiometric to the amount of D-glucose. NADPH was measured by means of light absorbance.

Plasma sodium was measured by ion-selective electrodes using plasma specimens by applying an Ion Selective Electrode (ISE) which makes use of the unique properties of certain membrane materials to develop an electrical potential (electromotive force, EMF) for the measurements of ions in solution (COBAS Integra 400; Roche Diagnostics GmbH, Mannheim, Germany, Assay: "ISE indirect Na—K—Cl for Gen.2").

Hemoglobin (Hb) was measured using the Reflotron® Hemoglobin assay. The test is based on the oxidation of hemoglobin to methemoglobin by potassium hexacyanoferrate (III) ($Fe^{2+}$ to $Fe^{3+}$). The hemoglobin level is proportional to the color intensity and were measured at a wavelength of 567 nm and 37° C.

HbA1c (glycated hemoglobin, Glycohemoglobin) was measured by using a Roche in vitro test which allows for the quantitative determination of HbA1c on Roche/Hitachi cobas c systems (Assay: "Tina-quant Hemoglobin A1c Gen.3", Roche Diagnostics GmbH, Mannheim, Germany).

Prealbumin was measured by using a Roche in vitro test which allows for the quantitative determination of prealbumin in human samples on Roche/Hitachi cobas c systems (ACN 710, ACN 8710). The assay is an immunoturbidimetric assay. Human prealbumin forms a precipitate with a specific antiserum which is determined turbidimetrically.

Cystatin C was measured by using an immunoturbidimetric assay for the quantitative in vitro determination of cystatin C in human serum and plasma on Roche automated clinical chemistry analyzers (Assay: Tina-quant Cystatin C, Roche Diagnostics GmbH, Mannheim, Germany). In this assay human cystatin C agglutinates with latex particles coated with anti-cystatin C antibodies. The aggregate is determined turbidimetrically at 546 nm.

CONCLUSIONS

The combination of NT-proBNP or BNP with other markers and clinical parameters can be used for monitoring purposes and as a guide for therapy in addition to current standard-of-care to adjust and titrate therapy in HF patients (chronic or acute HF after stabilization), preferably in those patients in whom HF is due to impaired systolic function. These markers and parameters are preferably Creatinine, eGFR (calculated from Creatinine levels), BUN, Glucose, HbA1c, hsCRP, Cystatin C, IL-6, Prealbumin, sFLt-1, Uric Acid, GFD-15, sST2, Galectin-3, Endostatin, Mimecan, IGFBP-7, Osteopontin, Sodium, Hemoglobin, and Hematocrit, as well as heart rate and QRS duration. Specifically, addition of these measurements to NT-proBNP or BNP together with current standard-of-care are able to further risk stratify HF patients who are already guided by NT-proBNP but may be in need for more intensified therapy and closer observation. Thus, the present invention optimizes heart failure therapy guidance beyond NT-proBNP by considering combinations of natriuretic peptides with other markers and/or clinical parameters.

The invention claimed is:

1. A method for diagnosing and treating a patient who is eligible for an intensification of heart failure therapy, said method comprising the steps of
    (a) measuring the level of at least one marker selected from the group consisting of creatinine, urea, sodium, glucose, HbA1c (glycated hemoglobin), hemoglobin, and hematocrit in a sample from a patient who has heart failure and who receives B-type natriuretic peptide (BNP) and/or N-terminal pro B-type natriuretic peptide (NT-proBNP) guided heart failure therapy,
    (b) comparing the level (or levels) of the marker (or markers) measured in (a) to a reference level (or reference levels),
    (c) identifying a patient who is eligible for an intensification of heart failure therapy based on the results of step b), and
    (d) intensifying heart therapy for subjects who have been identified in step (c)
wherein the heart failure therapy is medicinal heart failure therapy that comprises administration of at least one medicament selected from the group consisting of diuretics, angiotensin converting enzyme inhibitors, angiotensin II receptor blockers, beta blockers and aldosterone antagonists.

2. The method according to claim 1, further comprising step (c) of identifying a patient who is eligible for an intensification of heart failure therapy, or not.

3. The method of claim 1, wherein the patient displays a level of a BNP or NT-proBNP which is below the reference level for being indicative of intensification of heart failure therapy.

4. The method of claim 1, wherein
    i) the at least one marker is selected from the group consisting of creatinine, urea, glucose, and HbA1c (glycated hemoglobin), and wherein a level (or levels) of the at least one marker in the sample from the patient which is (are) above the reference level (reference levels) for said marker (markers) indicates that the patient is eligible for intensification of heart failure therapy, and/or wherein a level (or levels) of the at least one marker in the sample from the patient which is below the reference level (reference levels) for said marker (markers) indicate(s) that the patient is not eligible for intensification of heart failure therapy, and/or
    ii) the at least one marker is selected from the group consisting of sodium, hemoglobin, and hematocrit, and wherein a level (or levels) of the at least one marker in the sample from the patient which is (are) below the reference level (reference levels) for said marker (markers) indicate(s) that the patient is eligible for intensification of heart failure therapy, and/or wherein a level (levels) of the at least one marker in the sample from the patient which is above the reference level (reference levels) for said marker (markers) indicate(s) that the patient is not eligible for intensification of heart failure therapy.

5. A method for identifying a patient who is eligible for an intensification of heart failure therapy, said method comprising the steps of
    (a) measuring the level of a BNP or NT-proBNP in a sample from a patient who has heart failure and who receives BNP or NT-proBNP guided heart failure therapy;
    (b) measuring the level of at least one marker selected from the group consisting of creatinine, urea, sodium, glucose, HbA1c (glycated hemoglobin), hemoglobin, and hematocrit, in a sample from the patient, (c) comparing the level of the BNP or NT-proBNP measured in (a) to a reference level (or reference levels),
(d) comparing the level (or levels) of the at least one marker measured in (b) to a reference level (or reference levels), and
(e) identifying a patient who is eligible for an intensification of heart failure therapy based on the results of steps (c) and (d),
(f) intensifying heart therapy for the patient identified in step (e), wherein the heart failure therapy is medicinal heart failure therapy that comprises administration of at least one medicament selected from the group consisting of diuretics, angiotensin converting enzyme inhibitors, angiotensin II receptor blockers, beta blockers and aldosterone antagonists wherein the measuring step (b) is performed by combining the sample with one or more detectable antibodies specific for the BNP or NT-proBNP and detecting binding between the BNP or NT-proBNP and the respective antibody.

6. The method of claim 5, wherein
  i) the at least one marker is selected from the group consisting of creatinine, urea, glucose, and HbA1c (glycated hemoglobin), and wherein
    (a) a level of the at least one marker in the sample from the patient which is above the reference level for said marker, and a level of BNP or NT-proBNP which is above the reference level for said BNP or NT-proBNP is indicative for a patient who is eligible for intensification of heart failure therapy,
    (b) a level of the at least one marker in the sample from the patient which is above the reference level for said marker, and a level of said BNP or NT-proBNP which is below the reference level for said BNP or NT-proBNP is indicative for a patient who is eligible for intensification of heart failure therapy,
    (c) a level of the at least one marker in the sample from the patient which is below the reference level for said marker, and a level of said BNP or NT-proBNP which is above the reference level for said BNP or NT-proBNP is indicative for a patient who is eligible for intensification of heart failure therapy, and/or
    (d) a level of the at least one marker in the sample from the patient which is below the reference level for said marker, and a level of said BNP or NT-proBNP which is below the reference level for said BNP or NT-proBNP is indicative for a patient who is not eligible for intensification of heart failure therapy, and/or
  ii) the at least one marker is selected from the group consisting of sodium, hemoglobin, and hematocrit, and wherein
    (a) a level of the at least one marker in the sample from the patient which is below the reference level for said marker, and a level of said BNP or NT-proBNP which is above the reference level for said BNP or NT-proBNP is indicative for a patient who is eligible for intensification of heart failure therapy,
    (b) a level of the at least one marker in the sample from the patient which is below the reference level for said marker, and a level of said BNP or NT-proBNP which is below the reference level for said BNP or NT-proBNP is indicative for a patient who is eligible for intensification of heart failure therapy,
    (c) a level of the at least one marker in the sample from the patient which is above the reference level for said marker, and a level of said BNP or NT-proBNP which is above the reference level for said BNP or NT-proBNP is indicative for a patient who is eligible for intensification of heart failure therapy, and/or
    (d) a level of the at least one marker in the sample from the patient which is above the reference level for said marker, and a level of said BNP or NT-proBNP which is below the reference level for said BNP or NT-proBNP is indicative for a patient who is not eligible for intensification of heart failure therapy.

7. The method of claim 1, wherein the patient has heart failure classified as stage B or C according to ACC/AHA classification, and/or wherein the patient has heart failure according to class II or III of NYHA classification.

8. The method of claim 1, wherein the sample is a blood, serum or plasma sample, and/or wherein the patient is human.

9. The method of claim 1, wherein the heart failure therapy comprises combined administration of a beta blocker and an ACE inhibitor.

10. The method of claim 1, wherein the intensification of heart failure therapy comprises increasing the dosage of previously administered medicaments, the administration of a one or more further medicaments, life style changes, and combinations thereof.

* * * * *